(12) United States Patent
Sokol et al.

(10) Patent No.: US 10,543,386 B2
(45) Date of Patent: Jan. 28, 2020

(54) SYSTEMS AND METHODS FOR RESPIRATORY HEALTH MANAGEMENT

(71) Applicant: Advanced Ventilation Applications, Inc., Menlo Park, CA (US)

(72) Inventors: Eric R. Sokol, Menlo Park, CA (US); Jan Liphardt, Menlo Park, CA (US); Robert T. Chang, Menlo Park, CA (US)

(73) Assignee: ADVANCED VENTILATION APPLICATIONS, INC., Menlo Park, CA (US)

( * ) Notice: Subject to any disclaimer, the term of this patent is extended or adjusted under 35 U.S.C. 154(b) by 0 days.

(21) Appl. No.: 16/041,401

(22) Filed: Jul. 20, 2018

(65) Prior Publication Data

US 2018/0325422 A1 Nov. 15, 2018

Related U.S. Application Data

(63) Continuation of application No. PCT/US2017/015816, filed on Jan. 31, 2017.
(Continued)

(51) Int. Cl.
*A61B 5/08* (2006.01)
*A62B 9/00* (2006.01)
(Continued)

(52) U.S. Cl.
CPC .............. *A62B 9/006* (2013.01); *A61B 5/082* (2013.01); *A61B 5/091* (2013.01); *A61B 5/6819* (2013.01);
(Continued)

(58) Field of Classification Search
CPC ....... A61B 5/097; A61B 5/091; A61B 5/7275; A62B 7/10; A62B 23/06; A62B 9/006;
(Continued)

(56) References Cited

U.S. PATENT DOCUMENTS

| 855,573 A | 6/1907 | Albert |
| 4,384,925 A | 5/1983 | Stetter et al. |

(Continued)

FOREIGN PATENT DOCUMENTS

| CN | 1821779 A | 8/2006 |
| CN | 101375156 A | 2/2009 |

(Continued)

OTHER PUBLICATIONS

EP17748012.6 Extended European Search Report dated Sep. 12, 2019.
(Continued)

*Primary Examiner* — Navin Natnithithadha
*Assistant Examiner* — Andrey Shostak
(74) *Attorney, Agent, or Firm* — Wilson Sonsini Goodrich & Rosati

(57) ABSTRACT

Systems and methods for respiratory health management are provided. An air filtration and analysis system may comprise an apparatus configured to be worn by a user. The apparatus may comprise a filtration device. The system may also include a plurality of sensors configured to collect data. A portion of the sensor data may be indicative of (i) one or more characteristics of the air inhaled and/or exhaled by the user, and/or (ii) an environment in which the user is located. At least one sensor and/or the apparatus may be in communication with a processor that is configured to analyze the collected sensor data.

27 Claims, 24 Drawing Sheets

Related U.S. Application Data

(60) Provisional application No. 62/289,457, filed on Feb. 1, 2016, provisional application No. 62/289,546, filed on Feb. 1, 2016, provisional application No. 62/289,445, filed on Feb. 1, 2016, provisional application No. 62/289,480, filed on Feb. 1, 2016.

(51) Int. Cl.
| | |
|---|---|
| *A62B 7/10* | (2006.01) |
| *G16H 50/30* | (2018.01) |
| *A61B 5/00* | (2006.01) |
| *A61B 5/091* | (2006.01) |
| *A62B 23/06* | (2006.01) |

(52) U.S. Cl.
CPC .............. *A61B 5/7275* (2013.01); *A62B 7/10* (2013.01); *G16H 50/30* (2018.01); *A61M 2230/005* (2013.01); *A62B 23/06* (2013.01); *Y02A 50/20* (2018.01); *Y02A 50/24* (2018.01); *Y02A 50/241* (2018.01)

(58) Field of Classification Search
CPC ........ G16H 50/30; Y02A 50/20; Y02A 50/24; Y02A 50/241; A61M 2230/005
See application file for complete search history.

(56) References Cited

U.S. PATENT DOCUMENTS

| | | | | |
|---|---|---|---|---|
| 6,930,439 | B2 | 8/2005 | Wierach | |
| 9,075,007 | B2 | 7/2015 | McKendree | |
| 9,084,859 | B2 | 7/2015 | Connor | |
| 2001/0047127 | A1* | 11/2001 | New, Jr. ............... | A61B 5/0002 600/300 |
| 2002/0074000 | A1 | 6/2002 | Benda | |
| 2003/0106556 | A1 | 6/2003 | Alperovich et al. | |
| 2006/0189863 | A1* | 8/2006 | Peyser ................. | A61B 5/0031 600/345 |
| 2008/0035145 | A1* | 2/2008 | Adams .................. | A62B 18/08 128/204.18 |
| 2008/0041138 | A1 | 2/2008 | Marra | |
| 2009/0115654 | A1* | 5/2009 | Lo .......................... | F41G 7/008 342/62 |
| 2013/0104733 | A1 | 5/2013 | Bangera et al. | |
| 2013/0125617 | A1 | 5/2013 | Gouma et al. | |
| 2014/0155773 | A1* | 6/2014 | Stamatopoulos ...... | A61B 7/003 600/529 |
| 2014/0275857 | A1* | 9/2014 | Toth ...................... | A61B 5/087 600/301 |
| 2015/0138556 | A1 | 5/2015 | Leboeuf et al. | |
| 2015/0212057 | A1 | 7/2015 | Darveau | |
| 2015/0314144 | A1 | 11/2015 | Virr et al. | |
| 2015/0343245 | A1 | 12/2015 | Nozaki | |
| 2016/0121144 | A1* | 5/2016 | Hyde .................... | A62B 7/10 128/206.11 |
| 2016/0256715 | A1 | 9/2016 | Chao et al. | |

FOREIGN PATENT DOCUMENTS

| | | |
|---|---|---|
| CN | 102192927 A | 9/2011 |
| CN | 103412086 A | 11/2013 |
| CN | 104014087 A | 9/2014 |
| CN | 102665249 B | 5/2015 |
| CN | 104931101 A | 9/2015 |
| CN | 105148421 A | 12/2015 |
| DE | 10051784 C1 | 8/2002 |
| TW | M501266 U | 5/2015 |
| WO | WO-2017136336 A1 | 8/2017 |

OTHER PUBLICATIONS 7 million premature deaths annually linked to air pollution. (Press Release.) Mar. 25, 2014. 3 pages. Retrieved Oct. 18, 2018 from URL: <http://www.who.int/mediacentre/news/releases/2014/air-pollution/en/>.

Air Pollution. (Website.) World Health Organization. 4 pages. Retrieved Oct. 18, 2018 from URL: <http://www.who.int/airpollution/en/>.

Gupta et al. Characterizing exhaled airflow from breathing and talking. 20(1):31-39 (Feb. 2010). First published Jan. 7, 2010. DOI:https://doi.org/10.1111/j.1600-0668.2009.00623.x.

Ji et al. Piezoelectric Wind-Energy-Harvesting Device with Reed and Resonant Cavity. Jpn J Appl Phys 49:050204. 3 pages. (2010). Published online May 6, 2010. DOI: 10.1143/JJAP.49.050204.

Liu et al. Transparent air filter for high-efficiency PM2.5 capture. Nature Communications 6:6205 (Feb. 16, 2015). 9 pages. DOI: 10.1038/ncomms7205.

Particle Sensors, PPD42NJ and PPD2OV, Summary/How It Works. (Web page.) Shinyei Technology. Retrieved Oct. 23, 2018 from URL: <https://www.shinyei.co.jp/stc/eng/optical/main_dust.html>.

PCT/US2017/015816 International Search Report and Written Opinion dated Jul. 11, 2017.

Priya et al. Piezoelectric Windmill: A Novel Solution to Remote Sensing. Japanese Journal of Applied Physics 44(3):L104-L107 (2005). DOI: 10.1143/JJAP.44.L104.

Sharma et al. Sensor Faults: Detection Methods and Prevalence in Real-World Datasets. ACM Transactions on Sensor Networks. 6(3). 34 pages. (2010). DOI: 10.1145/1754414.1754419.

Smog—Who Does It Hurt? United States Environmental Protection Agency. EPA-452/K-99-001. 10 pages. (Jul. 1999.) Retrieved Oct. 18, 2018 from URL: <http://www3.epa.gov/airnow/health/smog.pdf>.

St. Clair et al. A scalable concept for micropower generation using flow-induced self-excited oscillations. Appl Phys Lett 96:144103 (2010). Published online Apr. 8, 2010. 3 pages. DOI: https://doi.org/10.1063/1.3385780.

Starner. Human-powered wearable computing. IBM Systems Journal 35(3-4). 12 pages. (1996).

Sun et al. PVDF microbelts for harvesting energy from respiration. Energy Environ Sci, 4:4508-4512 (2011). DOI: 10.1039/c1ee02241e.

* cited by examiner

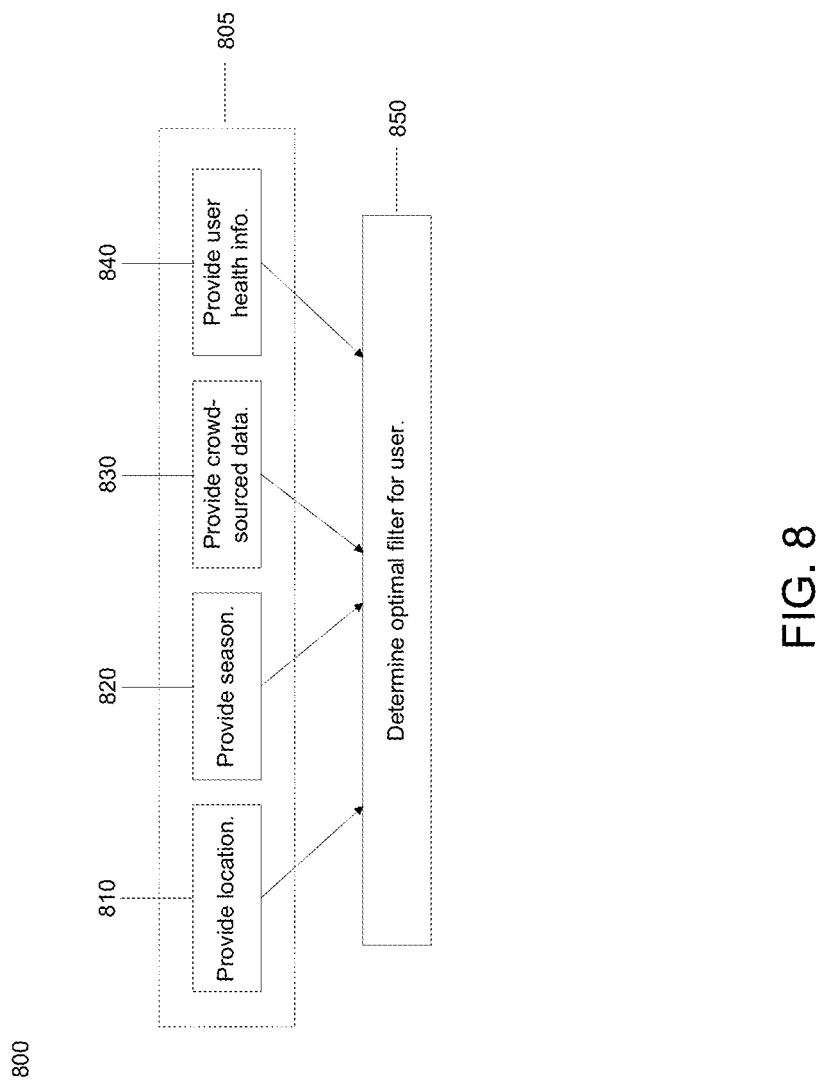

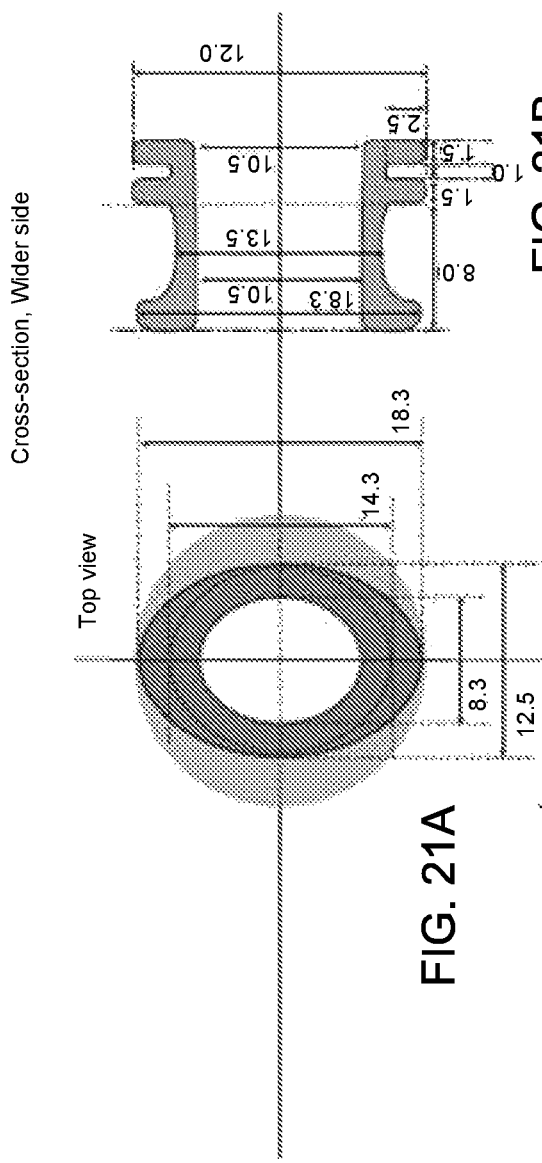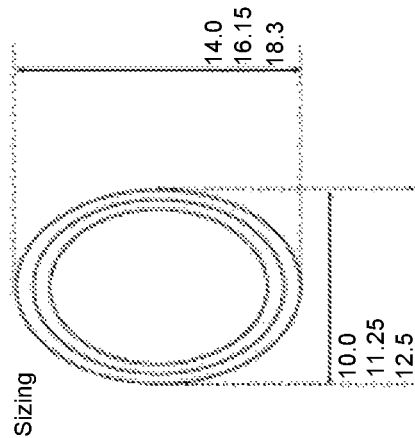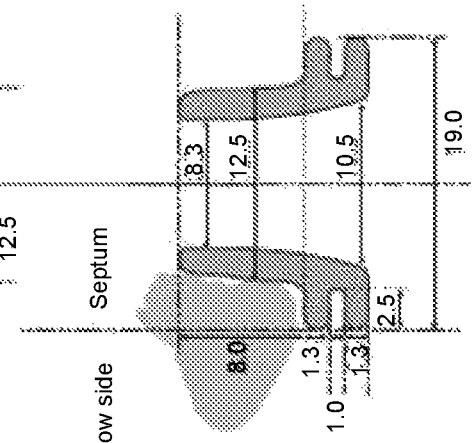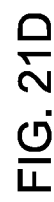
FIG. 21A
FIG. 21B
FIG. 21C
FIG. 21D

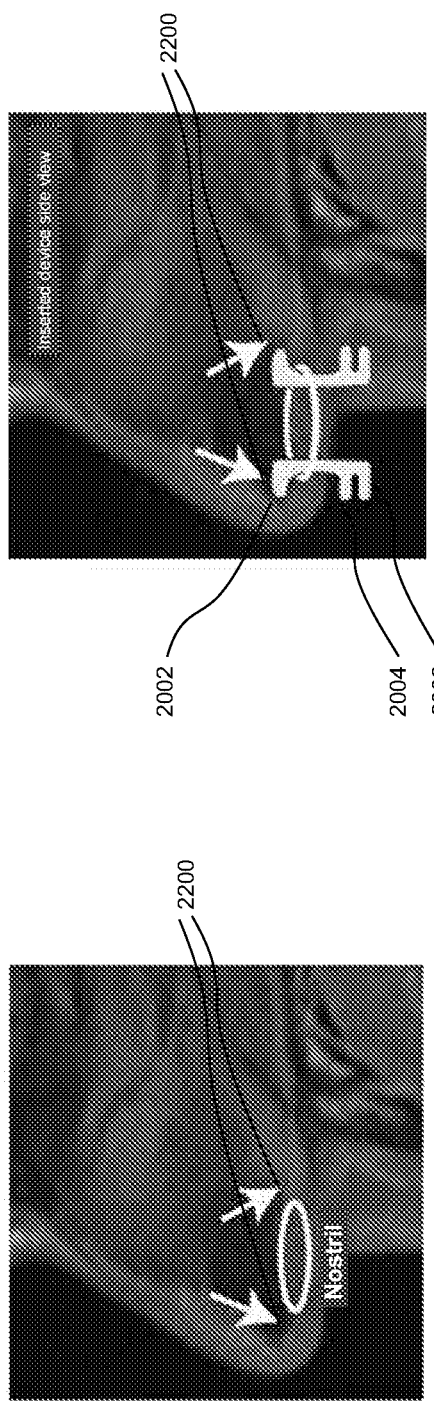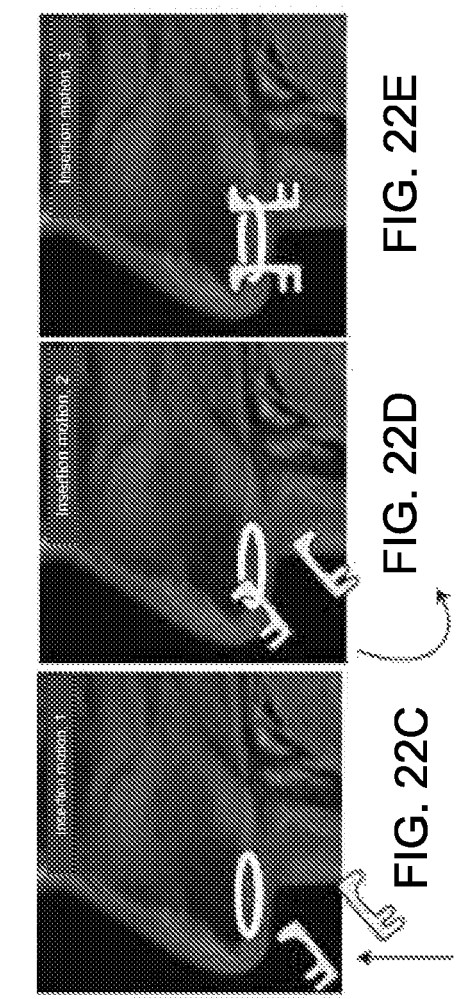

SYSTEMS AND METHODS FOR RESPIRATORY HEALTH MANAGEMENT

CROSS-REFERENCE

This application is a continuation application of PCT/US2017/015816, filed on Jan. 31, 2017, which claims the benefit of U.S. Provisional Patent Application No. 62/289,445, filed Feb. 1, 2016; U.S. Provisional Patent Application No. 62/289,457, filed Feb. 1, 2016; U.S. Provisional Patent Application No. 62/289,480, filed Feb. 1, 2016; and U.S. Provisional Patent Application No. 62/289,546, filed Feb. 1, 2016, which applications are incorporated herein by reference in their entireties for all purposes.

BACKGROUND

According to the United States Environmental Protection Agency (EPA), air pollutants can cause numerous negative health impacts, such as nose and throat discomfort, headache, allergic airway and skin reactions, dizziness, trouble breathing, coughing, pain, and reduced lung function. According to the World Health Organization (WHO), air pollutants of major health concern include bacteria and viruses (e.g. influenza strain H1N1), cigarette smoke, radon, particulate matter, carbon monoxide, ozone, nitrogen dioxide and sulfur dioxide. Outdoor and indoor air pollution often cause respiratory and other diseases, which can be fatal. In 2012, according to the World Health Organization, one in eight of total global deaths were the result of air pollution exposure. This finding more than doubles previous estimates and confirms that air pollution is now the world's largest single environmental health risk. The major causes of death due to air pollution are ischemic heart disease (40%), stroke (40%), chronic obstructive pulmonary disease (COPD) (11%), lung cancer (6%), and acute lower respiratory infections in children (3%). The air we inhale and exhale also contains chemicals that may not be harmful, but may be perceived to be unpleasant, such as pet odors or food smells. Health and performance relevant parameters include breathing rate, breathing volume, gas temperature and humidity, and the levels of gasses and chemicals, such as oxygen and carbon dioxide, in the exhaled air.

Air filtration devices can be used to mitigate the adverse health effects of airborne particulate matter, pathogens, allergens, and other pollutants. Some of these devices may be provided, for example, as masks that are worn over a person's mouth and/or nose. Most of these devices are passive filters that are designed to filter out a generic set of pollutants. These devices generally are not customized for each user's needs. Given their passive nature, these devices are also not configured to sense and adapt to changes in environmental conditions and/or a user's health conditions. In terms of aesthetics and ease of use, the bulk of these devices are typically unattractive and hinder the user's ability to communicate, as they are usually worn over a large part of the face.

In light of the above, there is a need for systems and methods that can accurately sense the surrounding environment and monitor users' health and health conditions, and that provide improved filtering performance for individual users. There is also a need for air filtration/respiratory devices that are effective, comfortable, easy to use by people suffering from various impairments, compact, aesthetically pleasing, can notify users of air pollution hazards and/or recommend certain corrective actions to users to improve their health and/or well-being, and that do not hinder a user's ability to communicate with others.

SUMMARY

The systems and methods described herein relate to the filtration and/or sensing of the air inhaled and/or exhaled by a user. The air that we inhale may contain numerous substances that are unpleasant or harmful. The systems and methods described herein may allow partial or complete filtration of these substances during inhalation, mitigating the harmful effects that these substances cause to a user's health. The systems and methods may allow users to obtain a customized filtration performance (such as a high level of filtration toward one or more harmful substances, a low level of filtration, or even a complete lack of filtration) based on the user's health concerns (such as allergies or residence in highly-polluted areas) or personal preferences (such as athletic performance). The systems and methods may comprise replaceable filter modules that allow for the easy replacement of filters, such as when a filter suffers from reduced performance due to extensive use or when a user's filtration needs or desires change.

Meanwhile, the air that we exhale can give significant insight into a person's current and future performance and health. The systems and methods described herein may allow the air exhaled by a user to be sensed and analyzed to provide information relevant to the health of a user. The sensing data may be utilized for the purposes health maintenance, prevention, and/or prediction. The sensing data may comprise information about the amount of a harmful substance to which a user is exposed. In some cases, the systems and methods described herein may both sense the air exhaled by a user and filter the air inhaled by the user. In other cases, the systems and methods may only sense the air exhaled by the user. In such cases, the sensing data may comprised information about the health status of a user. For instance, the sensing data may comprise information about vital signs of a user, such as the user's breathing rate. In some cases, the sensing data may serve to monitor the user for signs of sleep apnea or other sleeping disorders. In some cases, the sensing data may be used to predict the onset of asthma attacks. The sensing data may also be used to track the real-time performance of the filter, if the user's device includes such a filter.

The systems and methods described herein may notify users of actions that they can take to protect their health based on the sensing data and/or the filtration performance. For instance, the systems and methods may notify users that they are in areas of dangerously polluted air and tell them to go inside if they do not have adequate filtration. In some cases, the systems and methods may notify a user that they may soon have an asthma attack and provide suggestions for alleviating the symptoms, such as that the user should pre-emptively use their asthma inhaler. In some cases, the systems and methods may notify a user that they are displaying symptoms of sleep apnea and provide suggestions for reducing the severity of these symptoms.

In one aspect, an air filtration and analysis system comprises an apparatus configured to be worn by a user and a plurality of sensors configured to collect data. The apparatus may comprise a filtration device. A portion of the sensor data may be indicative of (i) one or more characteristics of the air inhaled and/or exhaled by the user, and/or (ii) an environment in which the user is located. At least one sensor and/or the apparatus may be in communication with a processor that is configured to analyze the collected sensor data. The filtration device may be configured to reduce one or more elements from the air inhaled by the user. The filtration device may be configured to be placed within the nasal passages of the user. The plurality of sensors may comprise chemical sensors, pressure and air flow sensors, heart-rate monitors, GPS sensors, temperature sensors, or inertial sensors. The plurality of sensors may comprise a first set of sensors that is located with or on the filtration device, and a second set of sensors that is located remote to the filtration device. The plurality of sensors may be configured to collect the sensor data at different predetermined sampling frequencies.

The processor may be configured to effect operation of the filtration system and/or at least one sensor based on the analyzed sensor data, so as to reduce an impact of one or more elements on the user's health. The processor may be configured to perform one or more of the following steps: (1) calibrate at least one sensor against a baseline sensor reference; (2) check whether at least one sensor is operating normally or whether the sensor is defective; or (3) correct for sensor drift, error or bias. The processor may be configured to analyze the sensor data by cross-checking an accuracy of each set of sensor data against other different types of sensor data. The processor may be configured to analyze the sensor data by correlating sensor data from different sources. The processor may configured to assign weights to the sensor data based on an accuracy and/or inherent sensing characteristics of each of the plurality of sensors. The processor may be configured to analyze the sensor data using statistical methods. The processor may be configured to analyze the sensor data by combining different sets of sensor data in a manner that compensates for the deficiencies of individual sensors or type of sensors.

The processor may be located on a mobile device or a wearable device that is carried or worn by the user, and/or on a server that is remote to the user. The processor may be configured to compress the collected sensor data and store the compressed data in a memory. The processor may be configured to effect the operation of the filtration device and/or the at least one sensor, by programming and customizing the filtration device and/or the at least one sensor (1) to meet the user's physiological needs and activities, and/or (2) based on the user's local environment. The processor may be configured to analyze the collected sensor data so to determine (1) a health status and/or medical conditions of the user, and/or (2) a type of activity that the user is performing. The processor may be configured to analyze the collected sensor data so as to determine the user's proximity to known sources of pollution, environment, time of day, and/or season. The processor may be configured to effect the operation of the filtration device and/or the at least one sensor, such that the filtration device and/or the at least one sensor is configured to dynamically and automatically adapt in real-time as the user moves from one location to another location, as time of day changes, as season changes, and/or depending on changes in the user's health status. The processor may be configured to effect the operation of the filtration device and/or the at least one sensor, by (1) selectively activating or de-activating the at least one sensor, and/or (2) adjusting a sensitivity level, sensing range, or sampling frequency of the at least one sensor.

In another aspect, a method for filtering and analyzing inhaled and/or exhaled air comprises obtaining data collected using a plurality of sensors, analyzing the collected sensor data, and effecting operation of the filtration device and/or at least one sensor of said plurality based on the analyzed sensor data. A portion of the sensor data may be indicative of (i) one or more characteristics of the air inhaled and/or exhaled by a user, and/or (ii) an environment in which the user is located. The filtration device may be configured to be worn by the user.

In another aspect, a system for filtering and analyzing inhaled and/or exhaled air comprises a server and a processor configured to execute a set of software instructions. The server may comprise a memory for storing data collected using a plurality of sensors operably coupled to a filtration device. A portion of the sensor data may be indicative of (i) one or more characteristics of the air inhaled and/or exhaled by a user, and/or (ii) an environment in which the user is located. The filtration device may be configured to be worn by the user. The processor may analyze the collected sensor data and effect operation of the filtration device and/or at least one sensor based on the analyzed sensor data.

In another aspect, a tangible computer readable medium stores instructions that, when executed by a processor, causes the processor to perform a computer-implemented method for filtering and analyzing inhaled and/or exhaled air. The method may comprise obtaining data collected using a plurality of sensors, analyzing the collected sensor data, and effecting operation of a filtration device and/or at least one sensor of said plurality based on the analyzed sensor data. A portion of the sensor data may be indicative of (i) one or more characteristics of the air inhaled and/or exhaled by a user, and/or (ii) an environment in which the user is located. The filtration device may be configured to be worn by the user.

In another aspect, a system for analyzing and displaying sensor data for pollution and user health monitoring comprises a processor in communication with a plurality of sensors. The processor may be configured to receive the sensor data collected by the plurality of sensors, analyze the collected sensor data to thereby generate a plurality of pollution and health metrics including a health recommendation that are specific to the user, and provide the plurality of pollution and health metrics on at least one user device. The plurality of sensors may comprise: (1) a first set of sensors located in proximity to a respiratory passageway of a user, and configured to collect sensor data associated with one or more elements in air inhaled by the user, and (2) a second set of sensors located remotely from the user and configured to collect a plurality of different sensor data. The plurality of pollution and health metrics may be configured to be displayed as a set of graphical visual objects on a graphical display of the user device.

The plurality of pollution and health metrics may include a detected level of the one or more elements in the air within the vicinity of the user. The plurality of pollution and health metrics may include a prediction of whether a level of the one or more elements is expected to increase or decrease within the vicinity of the user, and/or a rate of the increase or decrease. The health recommendation may include a warning of an impact to the user's health should the user continue to inhale the air containing the one or more elements. The health recommendation may include a numerical value that is indicative of a predicted impact of the one or more elements on the user's health. The health recommendation may include a suggested corrective action to minimize inhalation of the air containing the one or more elements. The suggested corrective action may include a recommendation that the user takes a different route or relocate to a different area. The suggested corrective action may include a recommendation that the user reduces or cease performing any strenuous physical activity. The suggested corrective action may include a recommendation that the user use an air filtration device that is configured to remove or reduce the one or more elements from the inhaled air.

The processor may be configured to generate an audio, visual and/or tactile signal to notify the user when the numerical value exceeds a predetermined threshold. The processor may be configured to generate an audio, visual and/or tactile signal to notify the user when a level of the one or more elements in the inhaled air exceeds a predetermined level. The processor may be configured to analyze the collected sensor data by correlating the user's medical or health condition to a level of the one or more elements in the inhaled air. The processor may be configured to analyze the collected sensor data so as determine which of the one or more elements have a greater impact or lesser impact to the user's health. The processor may be configured to adjust the health recommendation accordingly based on detected changes to the user's health. The processor may be configured to update the plurality of pollution and health metrics in real-time based on the collected sensor data.

In another aspect, a method of analyzing and displaying sensor data for pollution and user health monitoring comprises receiving the sensor data collected by a plurality of sensors and analyzing the collected sensor data to thereby generate a plurality of pollution and health metrics including a health recommendation that are specific to the user. The plurality of sensors may comprise: (1) a first set of sensors located in proximity to a respiratory passageway of a user, and configured to collect sensor data associated with one or more elements in air inhaled by the user, and (2) a second set of sensors located remotely from the user and configured to collect a plurality of different sensor data. The plurality of pollution and health metrics may be configured to be displayed as a set of graphical visual objects on a graphical display of at least one user device.

In another aspect, a tangible computer readable medium stores instructions that, when executed by a processor, causes the processor to perform a computer-implemented method for analyzing and displaying sensor data for pollution and user health monitoring. The method may comprise receiving the sensor data collected by a plurality of sensors, analyzing the collected sensor data to thereby generate a plurality of pollution and health metrics including a health recommendation that are specific to the user, storing the plurality of pollution and health metrics in a memory, and providing the plurality of pollution and health metrics on at least one user device. The plurality of sensors may comprise: (1) a first set of sensors located in proximity to a respiratory passageway of a user, and configured to collect sensor data associated with one or more elements in air inhaled by the user, and (2) a second set of sensors located remotely from the user and configured to collect a plurality of different sensor data. The plurality of pollution and health metrics may be configured to be displayed as a set of graphical visual objects on a graphical display of the user device.

In another aspect, an air filtration and sensing apparatus comprises a filtration device configured to be worn by a user, and configured to reduce one or more elements from air inhaled by the user, and a plurality of sensors operably coupled to the filtration device. The plurality of sensors may be configured to detect concentration levels of the one or more elements in the inhaled and/or exhaled air. At least of one sensor of said plurality may be powered by energy extracted from the user's motion and/or respiration.

The energy may be extracted using power generators comprising piezoelectric elements, inductive elements, and/or windmills. The apparatus may comprise an energy storage device configured to store and/or discharge the energy. The plurality of sensors may be configured to operate in a plurality of operational modes including a power saving mode and a performance mode. The performance mode may consume more power compared to the power saving mode. The apparatus may comprise one or more cooling mechanisms configured to improve heat dissipation from the plurality of sensors during operation of said sensors.

In another aspect, a method for powering at least one sensor in an air filtration and sensing apparatus comprises extracting, using one or more energy collection elements, energy from a user's motion and/or respiration and powering the at least one sensor selected from a plurality of a sensors using the extracted energy. The plurality of sensors may be configured to detect concentration levels of one or more elements in air inhaled and/or exhaled by the user. The plurality of sensors may be operably coupled to a filtration device. The filtration device may be configured to be worn by the user.

In another aspect, an air filtration apparatus comprises a filter holder configured to receive and interchange therein a plurality of different cartridge filters. The plurality of different cartridge filters may be configured to meet filtering requirements and health needs of different users for a plurality of different environments. The plurality of different cartridge filters may be configured to reduce one or more elements in the air inhaled by a user.

The filter holder may comprise a partial or full nasal insert. The filter holder may be part of a facial mask or respirator. The plurality of different cartridge filters may be configured to be interchanged and/or mounted onto the filter holder using a quick release mechanism. The plurality of different cartridge filters may be configured to be interchanged and/or mounted onto the filter holder without the use of tools. At least one of the cartridge filters may comprise a mesh. The mesh may comprise a nanofiber mat. The mesh may comprise activated carbon. The mesh may comprise a plurality of pores having the same or different shapes and/or sizes. The mesh may comprise a nanostructure mesh configured to allow for increased airflow. The mesh may be arranged in a manner such that filtration of air occurs in a predetermined direction during inhalation. The apparatus may comprise one or more dilation structures for increasing airflow. At least one of the filter cartridges may comprise a filtering element that is capable of adjusting its position and/or shape to increase airflow.

In another aspect, a method for assembling an air filtration apparatus comprises attaching a first cartridge filter into a filter holder of the air filtration apparatus, removing the first cartridge filter from the filter holder, and attaching a second cartridge filter into the filter holder. The filter holder may be configured to receive and interchange therein a plurality of different cartridge filters. The plurality of different cartridge filters may be configured to reduce one or more elements from air inhaled by a user. The first cartridge filter may be customized to meet a first set of filtering requirements and health needs of the user. The second cartridge filter may be customized to meet a second set of filtering requirements and health needs that are different from the first set of filtering requirements and health needs of the user.

In another aspect, a method of displaying sensor data for pollution and user health monitoring comprises receiving an input from a user on a user device and displaying, in response to the received input, the plurality of pollution and health metrics as a set of graphical visual objects on a graphical display. The input may comprise a request from the user associated with a plurality of pollution and health metrics including a health recommendation that are specific to the user. At least one of the graphical visual objects may be configured to change in real-time to reflect changes in the plurality of pollution and health metrics as the metrics are being monitored by a plurality of sensors. The user device may comprise a mobile device. The graphical display may be provided on the user device.

In another aspect, a nasal apparatus comprises a housing comprising a cavity located therein for permitting airflow into and out of a user's body and a retention mechanism configured to releasably couple the housing to a portion of the user's nasal passageway, so as to affix the nasal apparatus in place within the user's nose fin the user's nasal passages) using the retention mechanism, without requiring the use of one or more external fixation devices to secure the apparatus from outside of the user's nasal passages. The retention mechanism may be located on a peripheral portion of the housing. The retention mechanism may comprise at least one protrusion extending from the peripheral portion of the housing. The retention mechanism may comprise a first protrusion and a second protrusion that are located on opposite ends of the peripheral portion of the housing. The at least one protrusion may be configured to be releasably coupled to the portion of the user's nasal passageway. The at least one protrusion may be shaped to releasably couple to natural cartilage and/or tissue pockets located in the portion of the user's nasal passageway. The retention mechanism may be configured to releasably couple the housing to the portion of the user's nasal passageway via a predefined motion. The predefined motion pattern may comprise at least one rotary motion of the nasal apparatus. The apparatus may have a shape and/or profile that minimizes physical interference with lip movement of the user when the apparatus is being worn on the user's nose. The apparatus may not encroach on the user's upper lip when the apparatus is being worn on the user's nose. The apparatus may not visually obstruct lip movement of the user when the apparatus is being worn on the user's nose.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 shows a flowchart of a method of providing a user with a customized air filtration device.

FIG. 21A shows a top view of a nosebud that can be used in an air filtration and sensing device.

FIG. 21B shows a first cross-sectional view of the nosebud of FIG. 21A.

FIG. 21C shows a second cross-sectional view of the nosebud of FIG. 21A.

FIG. 21D shows exemplary dimensions of the nosebud of FIG. 21A.

FIG. 22A shows a magnetic resonance image (MRI) of pockets within the nose that may accept an air filtration and sensing device utilizing a nosebud.

FIG. 22B shows an air filtration and sensing device utilizing a nosebud that is anchored in the pockets of the nose.

FIG. 22C shows a first step of inserting an air filtration and sensing device utilizing a nosebud into the nose.

FIG. 2D shows a second step of inserting an air filtration and sensing device utilizing a nosebud into the nose.

FIG. 22E shows a third step of inserting an air filtration and sensing device utilizing a nosebud into the nose.

DETAILED DESCRIPTION

Figure 1A:
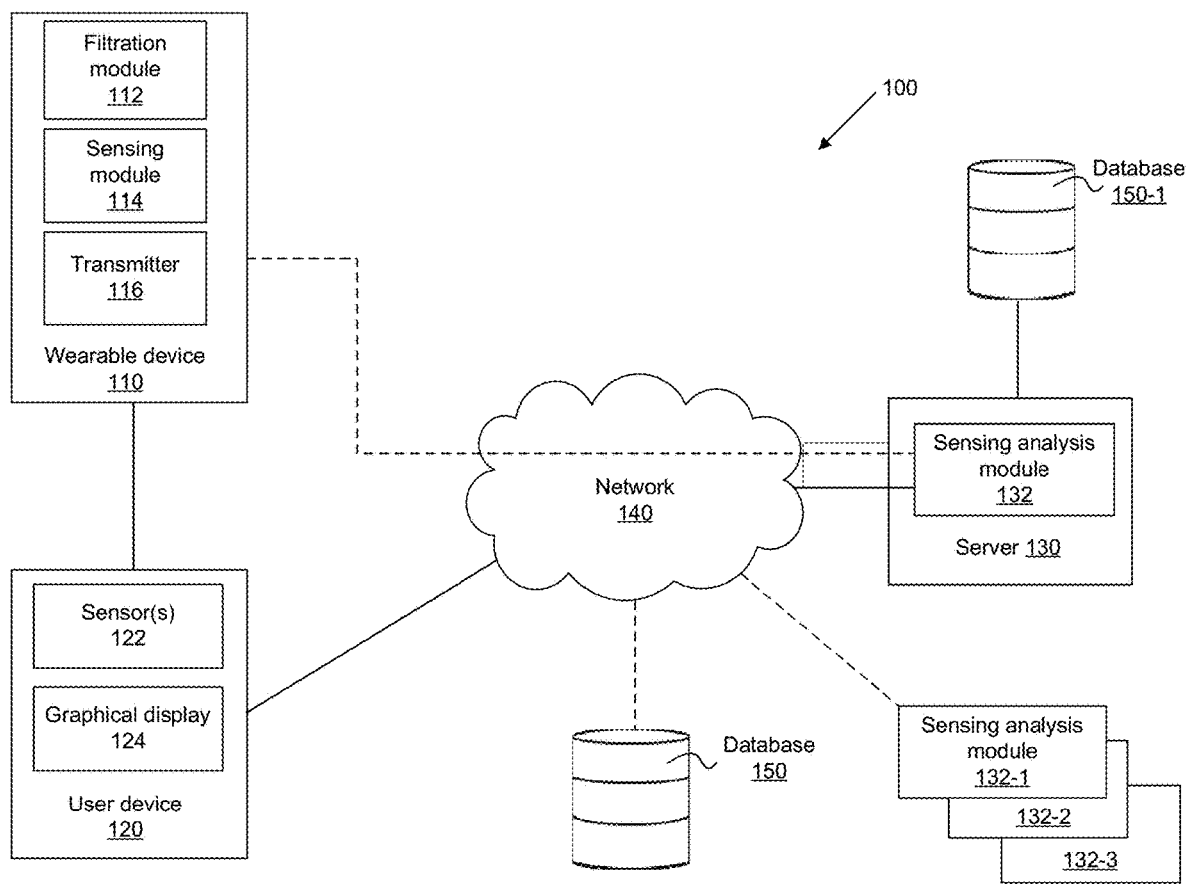
FIG. 1A shows a schematic of a system comprising one or more air filtration and sensing devices interacting within a network.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the term "pollution" or "pollutant" refers to a range of gases, chemicals, odors, particulate matter, and biological materials that may be detrimental and/or undesirable to human health upon inhalation, or that may be perceived to be unpleasant. Examples of pollutants include, but are not limited to radon, cigarette smoke, carbon monoxide (CO), carbon dioxide ($CO_2$), hydrocarbon compounds, fluorocarbon compounds, hydrofluorocarbon compounds, chlorofluorocarbon compounds, ozone ($O_3$) nitrous oxides ($NO_x$), sulfur-containing compounds, volatile organic compounds (VOCs) combustion-generated particulate matter such as soot, fine particulate matter with a diameter less than 2.5 μm (PM2.5), coarse particulate matter with a diameter between 2.5 μm and 10 μm (PM10), dander, plant pollens, bacteria, viruses, and pet odors. The term "pollution" or "pollutant" may refer to any material that may be detrimental to human health upon inhalation, or that may be perceived to be unpleasant, as is known to one having skill in the art.

As used herein, the term "air quality" refers to metrics based on one or more constituents of air that are associated with or statically correlated with human health effects and/or with a human's perception of the air. Metrics of air quality can be based on direct measurements of dust and particulate matter. Metrics of air quality can be based on measurements of proxies for particulate matter (e.g. gasses that are closely associated with particulate matter, such as carbon monoxide created during combustion). Metrics of air quality can be based on measurements of other constituents of air composition, such as plant pollen and/or moisture content. Metrics of air quality can include an air quality index (AQI) used by a government to indicate a relative air quality hazard level. For instance, the air quality index may be the United States Environmental Protection Agency's Air Quality Index, Canada's Air Quality Health Index, the Chinese Ministry of Environmental Protection's Air Pollution Index, the Indian Ministry for Environment, Forests and Climate Change's National Air Quality Index, Mexico City's Metropolitan Air Quality Index, Europe's Common Air Quality Index, or any other AQI as is known to one having skill in the art.

As used herein, the term "natural air flow" refers to air that is moving over or through the human body during the inhalation and exhalation cycle.

As used herein, the term "sensor" refers to a device that uses one or more electronic, chemical, mechanical, or optical means to convert the concentration of a compound (e.g. the amount of dust in the air) into a signal (typically, an electrical signal) that can be communicated to a microprocessor for further use, storage, and transmission.

As used herein, the term "sensor system" refers to a combination of circuit elements that together form a system capable of measuring, processing, storing, and/or transmitting one or more parameters. A sensor system may consist of one or more components taken from the following list: a power source, a power regulator, a microcontroller, a memory element, a signal conditioning element, a data logging element, a data transmission element, and one or more sensors.

The systems and methods disclosed herein relate to air filtration and sensing. The systems and methods may allow filtration and sensing of air composition and pollutants with compact devices that are capable of being worn in, on, or near the point at which air is inhaled (e.g. over the mouth or within the nasal passages). The devices may require a minimal supply of electrical power. The devices may also communicate the results of air composition measurements to a network, allowing advanced analysis of air composition results that are collected and/or aggregated from a large number of users. For instance, the analysis may comprise "big data" techniques. The analysis may produce information that is indicative of the pollution in an area, the type of pollutants that users are inhaling, the respiratory systems exhibited by users in a region, the demographics (such as age, sex, or profession) of users in a region, and/or the types of activity engaged in by users in a region. This information can be utilized to provide recommendations for corrective actions to be taken by a user in order to improve the user's health and wellbeing.

FIG. 1A shows a schematic of a system comprising one or more air filtration and sensing devices interacting with a data network. The air filtration and sensing system 100 may comprise a wearable air filtration and sensing device 110, a user device 120, a server 130 comprising a sensing analysis module 132, a network 140, and a database 150.

Each of the components 110, 120, 130, 132, and 150 may be operatively connected to one another via network 140 or any type of communication links that allows transmission of data from one component to another. The sensing analysis module may be configured to analyze input data from the user device and/or wearable device to detect and/or monitor air composition and pollution, and to provide information (e.g., recommendations) to assist a user in mitigating the effects of air pollution on the user's health. The sensing analysis module may be implemented anywhere within the system, and/or outside of the system. In some embodiments, the sensing analysis module may be implemented on the server. In other embodiments, the sensing analysis module may be implemented on the user device. Additionally, the sensing analysis module may be implemented on the wearable device. In some further embodiments, a plurality of sensing analysis modules may be implemented on one or more servers, user devices, and/or wearable devices. Alternatively, the sensing analysis module may be implemented in one or more databases. The sensing analysis module may be implemented using software, hardware, or a combination of software and hardware in one or more of the above-mentioned components within the system.

The wearable air filtration and sensing device 110 is configured to be worn by a user. For example, the device can be worn in, on, or near the point at which air is inhaled (e.g., within the nasal passage or over the mouth). The device 110 can be configured to obtain sensors readings of air pollution and composition and to filter the inhaled air. The wearable device may comprise a filtration module 112. The filtration module can filter the air to reduce the amount of pollutants passing from the atmosphere into the user's lungs, as described herein. The wearable device may also comprise a sensing module 114. The sensing module can detect and/or measure the presence and/or level of one or more chemicals or pollutants in a user's vicinity, as described herein. The wearable device may further comprise a transmitter 116. The transmitter can transmit various information to one or more user devices 120. Such information may include the type and/or level of pollutants in the user's vicinity, the user's health conditions, respiratory behavior, performance of the filtration module, reduction of pollutants from the inhaled air, etc. In some embodiments, the transmitter can transmit the information directly to the sensing analysis module on server 130 for analysis of the air pollution and/or the user's state of health.

The transmitter may be a wired transmitter. The transmitter may be a wireless transmitter. The transmitter may communicate information obtained by the sensing module via a wireless communication channel to one or more user devices 120. The user device may be a smartphone or any other portable electronic device. The wireless communication may be via Bluetooth communication. The wireless communication may be via Wi-Fi communication. The wireless communication may be via any other wireless communication known to one skilled in the art. In some cases, the air filtration and sensing device 110 may also include a receiver that is configured to receive information from the user device and/or other components in system 100 (e.g., sensing analysis module, server, database, etc.). In some embodiments, the transmitter may be replaced by a transceiver that is capable of providing two-way communication between the wearable device and other components within system 100.

The transmitter may transmit raw sensor data or processed sensor data. Some or all processing of the sensor data may be performed on the wearable device, user device, and/or sensing analysis module. For instance, any of the aforementioned components may comprise hardware or software elements that allow the sensor data obtained by the sensing module to be converted into electronic representations, and that can process the electronic representations to extract, for instance, measured values of the concentrations of the air pollutants. User device 120 may be a computing device configured to perform one or more operations consistent with the disclosed embodiments.

Examples of user devices may include, but are not limited to, mobile devices, smartphones/cellphones, tablets, personal digital assistants (PDAs), laptop or notebook computers, desktop computers, media content players, television sets, video gaming station/system, virtual reality systems, augmented reality systems, microphones, or any electronic device capable of analyzing, receiving, providing or displaying certain types of data (e.g., air pollution data, health impact, health recommendation, user's health status, etc.) to a user. The user device may be a handheld object. The user device may be portable. The user device may be carried by a human user. In some cases, the user device may be located remotely from a human user, and the user can control the user device using wireless and/or wired communications.

User device 120 may include one or more processors that are capable of executing non-transitory computer readable media that may provide instructions for one or more operations consistent with the disclosed embodiments. The user device may include one or more memory storage devices comprising non-transitory computer readable media including code, logic, or instructions for performing the one or more operations. The user device may include software applications that allow the user device to communicate with and transfer data between wearable device 110, server 130, sensing analysis module 132, and/or database 150. The user device may include a communication unit, which may permit the communications with one or more other components in system 100. In some instances, the communication unit may include a single communication module, or multiple communication modules. In some instances, the user device may be capable of interacting with one or more components in system 100 using a single communication link or multiple different types of communication links.

User device 120 may include a display. The display may be a screen. The display may or may not be a touchscreen. The display may be a light-emitting diode (LED) screen, OLED screen, liquid crystal display (LCD) screen, plasma screen, or any other type of screen. The display may be configured to show a user interface (UI) or a graphical user interface (GUI) rendered through an application (e.g., via an application programming interface (API) executed on the user device). The GUI may show images that permit a user to view various information relating to air pollution in the user's vicinity, performance of the filtration module, etc. The user device may also be configured to display webpages and/or websites on the Internet. One or more of the webpages/websites may be hosted by server 130 and/or rendered by sensing analysis module 132.

A user may navigate within the GUI through the application. For example, the user may select a link by directly touching the screen (e.g., touchscreen). The user may touch any portion of the screen by touching a point on the screen. Alternatively, the user may select a portion of an image with aid of a user interactive device (e.g., mouse, joystick, keyboard, trackball, touchpad, button, verbal commands, gesture-recognition, attitude sensor, thermal sensor, touch-capacitive sensors, or any other device). A touchscreen may be configured to detect location of the user's touch, length of touch, pressure of touch, and/or touch motion, whereby each of the aforementioned manners of touch may be indicative of a specific input command from the user.

User device 120 may include smartwatches, wristbands, glasses, gloves, headgear (such as hats, helmets, virtual reality headsets, augmented reality headsets, headmounted devices (HMD), headbands), pendants, armbands, leg bands, shoes, vests, motion sensing devices, etc. The wearable device may be configured to be worn on a part of a user's body (e.g., a smartwatch or wristband may be worn on the user's wrist). The user device may include one or more types of sensors. Examples of types of sensors may include inertial sensors (e.g., accelerometers, gyroscopes, and/or gravity detection sensors, which may form inertial measurement units (IMUs)), location sensors (e.g., global positioning system (GPS) sensors, mobile device transmitters enabling location triangulation), heart rate monitors, external temperature sensors, skin temperature sensors, capacitive touch sensors, sensors configured to detect a galvanic skin response (GSR), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses), pressure sensors (e.g., barometers), humidity sensors, vibration sensors, audio sensors (e.g., microphones), and/or field sensors (e.g., magnetometers, electromagnetic sensors, radio sensors).

User device 120 may further include one or more devices capable of emitting a signal into an environment. For instance, the user device may include an emitter along an electromagnetic spectrum (e.g., visible light emitter, ultraviolet emitter, infrared emitter). The user device may include a laser or any other type of electromagnetic emitter. The user device may emit one or more vibrations, such as ultrasonic signals. The user device may emit audible sounds (e.g., from a speaker). The user device may emit wireless signals, such as radio signals or other types of signals. The user device may emit smells and/or tastes (e.g., due to the release of a chemical). Some of the signals (e.g., audible sound, tactile signals, visual indicators, etc.) may be used to alert a user when the air pollution in the user's vicinity exceeds a predetermined threshold, and/or to inform the user to take certain corrective actions to mitigate the impact of air pollution on the user's health.

Wearable device 110 and user device 120 may be operated by one or more users consistent with the disclosed embodiments. In some embodiments, a user may be associated with a unique user device and a unique wearable device. Alternatively, a user may be associated with a plurality of user devices and wearable devices. A user as described herein may refer to an individual or a group of individuals who are seeking to improve their wellbeing using device 110. For example, a person or a group of persons suffering from allergies may wish to find relief from the allergen. A person or a group of persons living in a city with high levels of air pollution may wish to find relief from the air pollution. System 100 can determine each user's exposure to one or more pollutants, and reduce their exposure to those pollutants through the wearable devices (e.g., filtration module).

User device 120 may be configured to receive input from one or more users. A user may provide an input to the user device using an input device, for example, a keyboard, a mouse, a touchscreen panel, voice recognition and/or dictation software, or any combination of the above. The user input may include statements, comments, questions, or answers relating to a user's air filtration requirements. Different users may provide different inputs. The user input may be indicative of the user's health conditions. Some of the health conditions may be affected by air pollution.

Server 130 may be one or more server computers configured to perform one or more operations consistent with the disclosed embodiments. In one aspect, the server may be implemented as a single computer, through which wearable device 110 and user device 120 are able to communicate with sensing analysis module 132 and database 150. In some embodiments, the wearable device and/or the user device may communicate with the sensing analysis module directly through the network. In some embodiments, the server may communicate on behalf of the wearable device and/or the user device with the sensing analysis module or database through the network. In some embodiments, the server may embody the functionality of one or more of sensing analysis modules. In some embodiments, one or more sensing analysis modules may be implemented inside and/or outside of the server. For example, the sensing analysis modules may be software and/or hardware components included with the server or remote from the server.

In some embodiments, the wearable device and/or the user device may be directly connected to the server through a separate link (not shown in FIG. 1A). In certain embodiments, the server may be configured to operate as a front-end device configured to provide access to one or more sensing analysis modules consistent with certain disclosed embodiments. The server may, in some embodiments, utilize one or more sensing analysis modules to analyze input data from the wearable device and/or user device in order to detect and/or monitor a user's exposure to one or more pollutants, and to provide information (e.g., recommendations) to assist the user in managing their exposure to the pollutants. The server may also be configured to store, search, retrieve, and/or analyze data and information stored in one or more of the databases. The data and information may include raw data and derived vital signs collected from various sensors (such as global positioning sensors, heart rate monitors, inertial sensors, body temperature sensors, respiration rate sensors, gait sensors, etc.) on one or more user devices, as well as each user's historical exposure to pollutants. While FIG. 1A illustrates the server as a single server, in some embodiments, multiple devices may implement the functionality associated with a server.

A server may include a web server, an enterprise server, or any other type of computer server, and can be computer programmed to accept requests (e.g., HTTP, or other protocols that can initiate data transmission) from a computing device (e.g., user device and/or wearable device) and to serve the computing device with requested data. In addition, a server can be a broadcasting facility, such as free-to-air, cable, satellite, and other broadcasting facility, for distributing data. A server may also be a server in a data network (e.g., a cloud computing network).

A server may include known computing components, such as one or more processors, one or more memory devices storing software instructions executed by the processor(s), and data. A server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers.

While FIG. 1A illustrates the server as a single server, in some embodiments, multiple devices may implement the functionality associated with server.

Network 140 may be a network that is configured to provide communication between the various components illustrated in FIG. 1A. The network may be implemented, in some embodiments, as one or more networks that connect devices and/or components in the network layout for allowing communication between them. For example, wearable device 110, user device 120, and sensing analysis module 132 may be in operable communication with one another over network 140. Direct communications may be provided between two or more of the above components. The direct communications may occur without requiring any intermediary device or network. Indirect communications may be provided between two or more of the above components. The indirect communications may occur with aid of one or more intermediary device or network. For instance, indirect communications may utilize a telecommunications network. Indirect communications may be performed with aid of one or more router, communication tower, satellite, or any other intermediary device or network. Examples of types of communications may include, but are not limited to: communications via the Internet, Local Area Networks (LANs), Wide Area Networks (WANs), Bluetooth, Near Field Communication (NFC) technologies, networks based on mobile data protocols such as General Packet Radio Services (GPRS), GSM, Enhanced Data GSM Environment (EDGE), 3G, 4G, or Long Term Evolution (LTE) protocols, Infra-Red (IR) communication technologies, and/or Wi-Fi, and may be wireless, wired, or a combination thereof. In some embodiments, the network may be implemented using cell and/or pager networks, satellite, licensed radio, or a combination of licensed and unlicensed radio. The network may be wireless, wired, or a combination thereof.

Wearable device 110, user device 120, server 130, and/or sensing analysis module 132 may be connected or interconnected to one or more databases 150. The databases may be one or more memory devices configured to store data. Additionally, the databases may also, in some embodiments, be implemented as a computer system with a storage device. In one aspect, the databases may be used by components of the network layout to perform one or more operations consistent with the disclosed embodiments.

In one embodiment, the databases may comprise storage containing a variety of data sets consistent with disclosed embodiments. For example, the databases may include, for example, data collected by various sensors located on wearable device 110 and/or user device 120. The databases may also include users' preferences, historical exposure to one or more pollutants, and traits associated with exposure to the pollutant, changes and/or improvements in the users' lifestyles that lead to a reduction in exposure to the pollutant, the users' success at managing or overcoming exposure to the pollutant, etc. In some embodiments, the database(s) may include crowd-sourced data comprising air pollutant exposure information obtained from internet forums and social media websites. The Internet forums and social media websites may include personal and/or group blogs, Facebook™, Twitter™, etc. Additionally, in some embodiments, the database(s) may include crowd-sourced data comprising air pollutant exposure information, whereby this information may be directly input by one or more other users into the sensing analysis module(s). The crowd-sourced data may contain up-to-date or current information on air pollutant exposure, recommendations to reduce or avoid exposure to the pollutant, etc. The crowd-sourced data may be provided by other users who have experience with trying to reduce their exposure to pollutants.

In certain embodiments, one or more of the databases may be co-located with the server, may be co-located with one another on the network, or may be located separately from other devices (signified by the dashed line connecting the database(s) to the network). One of ordinary skill will recognize that the disclosed embodiments are not limited to the configuration and/or arrangement of the database(s).

Any of the wearable device, user device, server, sensing analysis module, and the database may, in some embodiments, be implemented as a computer system. Additionally, while the network is shown in FIG. 1A as a "central" point for communications between components, the disclosed embodiments are not so limited. For example, one or more components of the network layout may be interconnected in a variety of ways, and may in some embodiments be directly connected to, co-located with, or remote from one another, as one of ordinary skill will appreciate. Additionally, while some disclosed embodiments may be implemented on the server, the disclosed embodiments are not so limited. For instance, in some embodiments, other devices (such as sensing analysis modules(s) and/or database(s)) may be configured to perform one or more of the processes and functionalities consistent with the disclosed embodiments, including embodiments described with respect to the server.

Although particular computing devices are illustrated and networks described, it is to be appreciated and understood that other computing devices and networks can be utilized without departing from the spirit and scope of the embodiments described herein. In addition, one or more components of the network layout may be interconnected in a variety of ways, and may in some embodiments be directly connected to, co-located with, or remote from one another, as one of ordinary skill will appreciate.

The sensing analysis modules(s) may be implemented as one or more computers storing instructions that, when executed by processor(s), analyze input data from a user device and/or a wearable device in order to detect and/or monitor a user's exposure to one or more pollutants, and to provide information (e.g., recommendations) to assist the user in managing their exposure to such pollutants. The sensing analysis modules(s) may also be configured to store, search, retrieve, and/or analyze data and information stored in one or more databases. The data and information may include raw data collected from various sensors on one or more wearable devices and/or user devices, as well as each user's historical behavioral pattern and social interactions relating to exposure to the pollutants. In some embodiments, server 130 may be a computer in which the sensing analysis module is implemented.

However, in some embodiments, one or more sensing analysis modules(s) 132 may be implemented remotely from server 130. For example, a user device may send a user input to server 130, and the server may connect to one or more sensing analysis modules(s) 132 over network 140 to retrieve, filter, and analyze data from one or more remotely located database(s) 150. In other embodiments, the sensing analysis modules(s) may represent software that, when executed by one or more processors, perform processes for analyzing data to determine a user's exposure to one or more pollutants, and to provide information (e.g., recommendations) to assist the user in reducing their exposure to the pollutants.

A server may access and execute sensing analysis modules(s) to perform one or more processes consistent with the disclosed embodiments. In certain configurations, the sensing analysis modules(s) may be software stored in memory accessible by a server (e.g., in memory local to the server or remote memory accessible over a communication link, such as the network). Thus, in certain aspects, the sensing analysis modules(s) may be implemented as one or more computers, as software stored on a memory device accessible by the server, or a combination thereof. For example, a sensing analysis module (e.g., 132-1) may be a computer executing one or more air pollution sensing techniques, and another sensing analysis module (e.g., 132-2) may be software that, when executed by a server, performs one or more air pollution sensing techniques.

The air pollutant measurements may be performed at many locations. For instance, the measurements may be performed on wearable device. The measurements may be performed at a location near to the wearable device, such as by a smartphone or other portable electronic device. The measurements may be performed on the cloud-based storage, communications, and analysis system. The air filtration and sensing device may be configured to compress measurement data and transmit the compressed measurement data to the cloud-based storage, communications, and analysis system.

The functions of the sensing analysis module, and its communication with the wearable device and user device, will be described in detail below with reference to FIG. 2A.

Figure 1B:
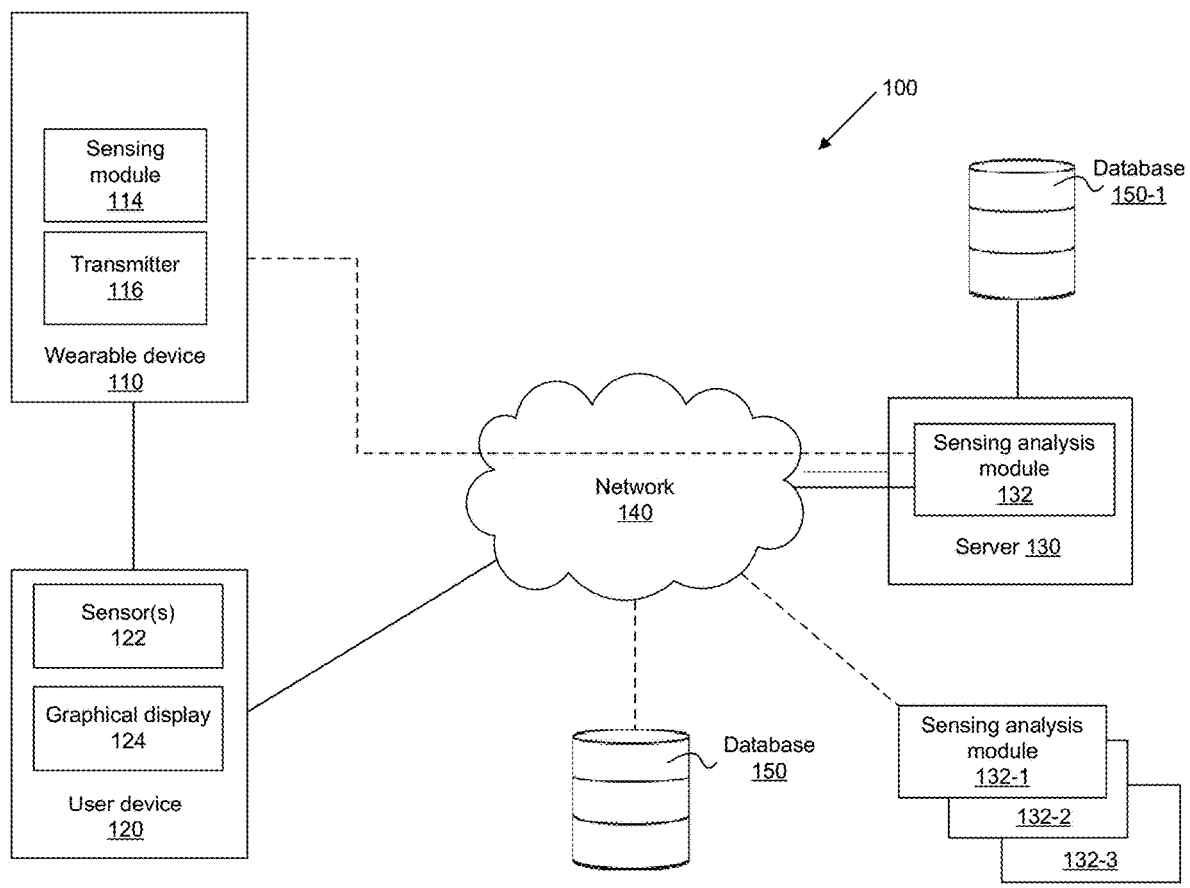
FIG. 1B shows a schematic of a system comprising one or more air sensing devices interacting within a network.

The invention as described herein need not be limited to air filtration, but may extend generally to the collection and analysis of respiratory health information to improve users' health and/or well-being. FIG. 1B shows a schematic of a system comprising one or more air sensing devices interacting within a network. The system may comprise the components of FIG. 1A, such as the wearable device, user device, server, network, and database. In contrast to the system of FIG. 1A, the system of FIG. 1B may comprise a wearable device that comprises only a sensing module 114 and transmitter 116. The wearable device of FIG. 1B need not include a filtration module, and may be utilized by users who do not require any air filtration capabilities. For instance, a user who lives in an area with low pollution and suffers from sleep apnea may utilize the sensing module to monitor their breathing during sleep, but may not require filtration of the air that they inhale.

Figure 2A:
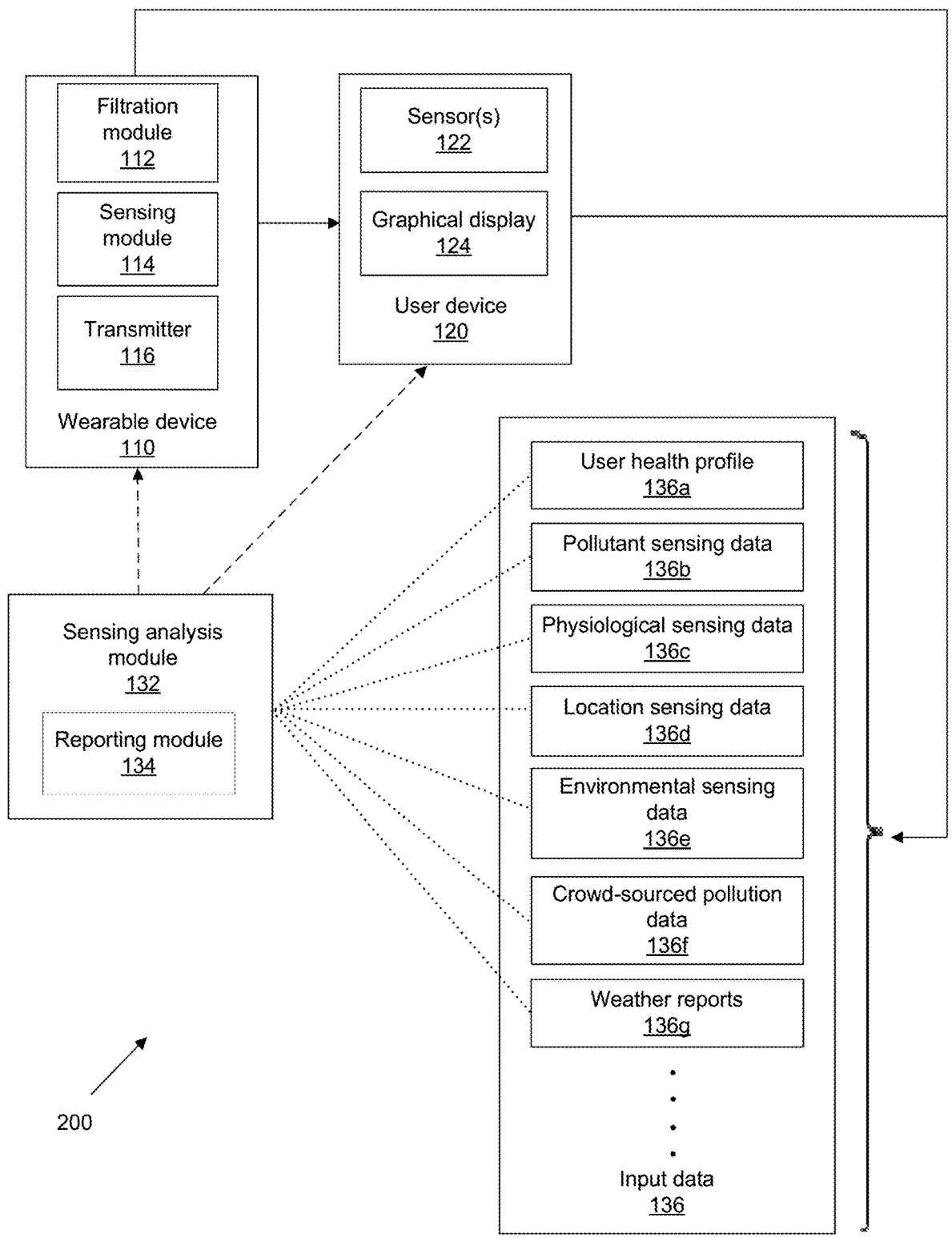
FIG. 2A illustrates exemplary components in an air filtration and sensing device.

FIG. 2A illustrates exemplary components in an air filtration and sensing system. Referring to FIG. 2A, a system 200 may comprise a wearable device 110, a user device 120, and a sensing analysis module 132. As previously described, the sensing analysis module may be implemented inside and/or outside of a server. For example, the sensing analysis module may be software and/or hardware components included with a server, or remote from the server. In some embodiments, the sensing analysis module (or one or more functions of the sensing analysis module) may be implemented on the wearable device. Alternatively, the wearable device, user device, and/or server may be configured to perform different functions of the sensing analysis module. Optionally, one or more functions of the sensing analysis module may be duplicated across the wearable device, user device, and/or server.

In the example of FIG. 2A, user device 120 may comprise at least one sensor 122. The sensor 122 may include location sensors (e.g., GPS receivers), heart rate monitors, inertial sensors (e.g., accelerometers and gyroscopes), etc. One or more other types of sensors as described elsewhere herein may be incorporated into the user device.

The user device and/or the wearable device may be configured to provide input data 136 to the sensing analysis module. The input data may comprise a user health profile 136a, pollutant sensing data 136b, physiological sensing data 136c, location sensing data 136d, environmental sensing data 136e, crowd-sourced pollution data 136f, weather reports 136g, etc.

The user health profile may be provided by a user via the user device. The user health profile may incorporate information about a user's medical conditions, prescribed and/or unprescribed medications, electronic health record data, or any other information that may be relevant to a user's health. The user health profile may be in response to questions provided by the sensing analysis modules. Examples of questions may include whether the user has certain health concerns such as allergies and an estimate of the levels of pollutants that the user has been exposed to in the recent past. The user's responses to those questions may be used to supplement the pollution sensing data to predict where/when the user is likely to be exposed to the pollutants. This information obtained from the user input can be analyzed using machine learning processes.

In some cases, the user health profile may be continuously updated in response to dynamically changing information provided by the user or obtained by the sensing module. For instance, the user health profile may initially comprise a baseline profile. The baseline profile may specify a user's health profile at an initial point in time. As time elapses, the user may modify elements of their health profile, such as by providing updated information about their health concerns. In other cases, the sensing module may note changes in the user's health profile, such as by sensing a change in the composition of air exhaled by the user. Such changes may be compared against the baseline and used to produce an updated user profile. In some cases, the user profile may be continuously updated in response to new information provided by the user or obtained by the sensing module. In some cases, "big data" techniques may be utilized to continuously update the user profile.

The pollutant sensing data may comprise raw data collected by one or more pollution sensors on the wearable device, as described herein. The pollutant sensing data may include, for example, the types of pollutants in the inhaled air present in the vicinity of the user, as well as the level of those detected pollutants. The pollutant sensing data may be stored in memory located on the wearable device, user device, and/or server. In some embodiments, the pollutant sensing data may be stored in one or more databases. The databases may be located on the server, wearable device, and/or user device. Alternatively, the databases may be located remotely from the server, wearable device, and/or user device.

The physiological sensing data may comprise data collected by one or more physiological sensors on the wearable device or user device. For instance, the physiological sensing data may comprise one or more measurements of a user's heart rate, breathing rate, respiratory behavior, blood pressure, glucose level, and/or any other physiological data.

The location sensing data may be determined by a location sensor (e.g., GPS receiver) on the wearable device and/or the user device. The user location may be used to determine places where the user is exposed to pollutants or is likely to be exposed to pollutants. The user location may also be used to supplement the pollution sensing data to determine the probability of future exposure to the pollutants. The sensing analysis module can be configured to map the pollutant sensing data to the detected locations.

The environmental sensing data may comprise data collected by one or more environmental sensors. The environmental sensing data may comprise information obtained from sources that track air pollutant levels, such as the National Weather Service (NWS) or National Oceanic and Atmospheric Administration (NOAA). The environmental sensing data can provide various types of environmental information. For example, the sensor data may be indicative of an environment type, such as an indoor environment, outdoor environment, low altitude environment, or high altitude environment. The sensor data may also provide information regarding current environmental conditions, including weather (e.g., clear, rainy, snowing), visibility conditions, wind speed, time of day, and so on. Furthermore, the environmental information collected by the sensors may include information regarding the objects in the environment, such as the number, density, geometry, and/or spatial disposition of objects in the environment. The amount of air pollution may be affected by the environmental type. For example, a location that is situated in a valley with low winds and a large number of factories may have higher air pollution compared to another location that is close to the sea with good air circulation.

The crowd-sourced information may comprise information relevant to determining a user's exposure to air pollutants. For instance, the crowd-sourced information may comprise information about current air pollutant levels at one or more locations, predicted future air pollutant levels at one or more locations, or any other information relevant to determining the user's exposure to air pollutants. The crowd-sourced information may comprise information obtained from websites or applications, such as newsfeeds, social media websites or applications. The crowd-sourced information may comprise information obtained from other devices utilized by other users.

The weather reports may comprise information obtained from local or network newscasts.

Figure 2B:
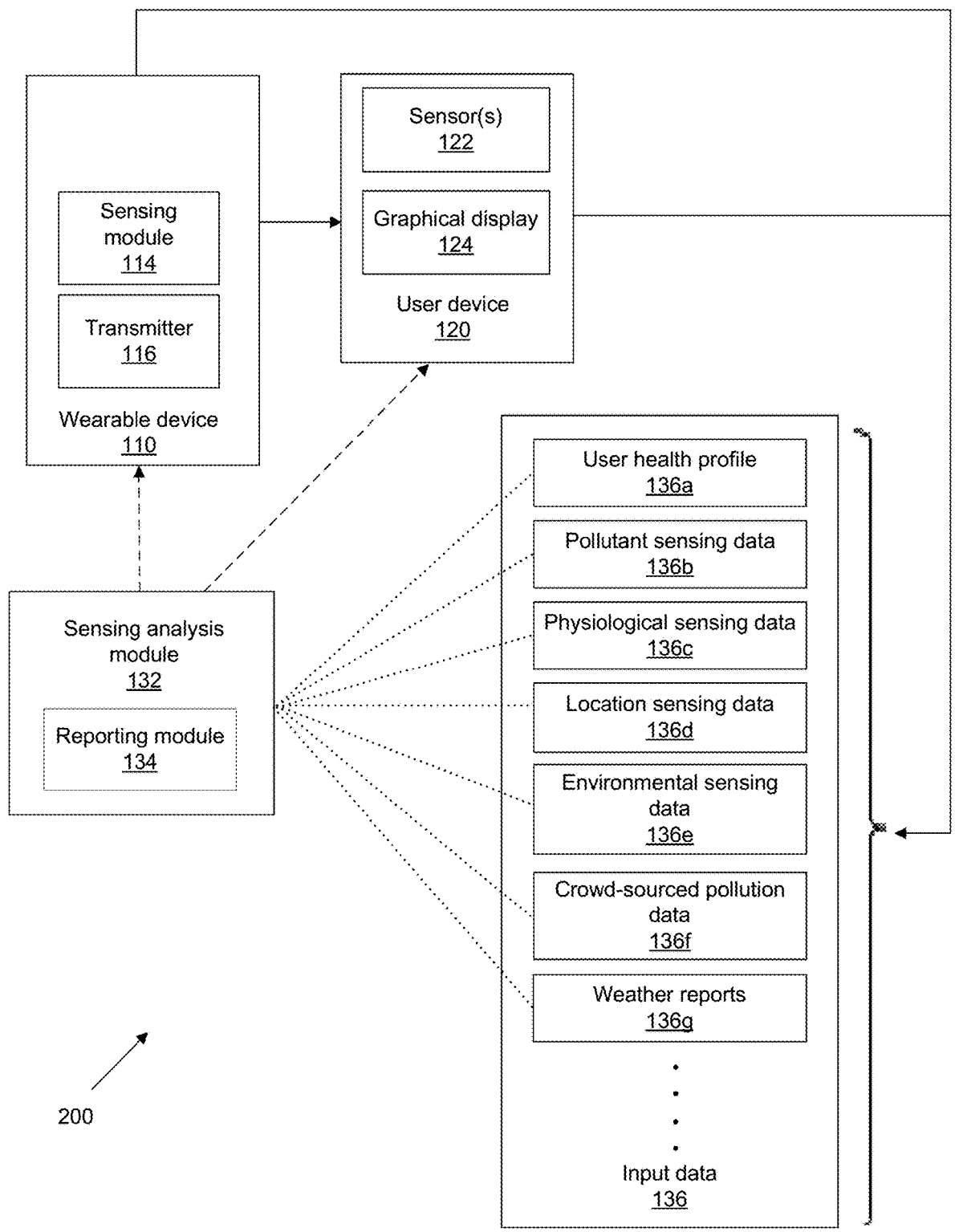
FIG. 2B illustrates exemplary components in an air sensing device.

FIG. 2B illustrates exemplary components in an air sensing system. The system may comprise all of the components of FIG. 2A. In contrast to the system of FIG. 2A, the system of FIG. 2B may comprise a wearable device that comprises only a sensing module 114 and transmitter 116. The wearable device of FIG. 2B need not include a filtration module, and may be utilized by users who do not require any air filtration capabilities. For instance, a user who lives in an area with low pollution and suffers from sleep apnea may utilize the sensing module to monitor their breathing but need not require filtration of the air that they inhale.

Figure 3:
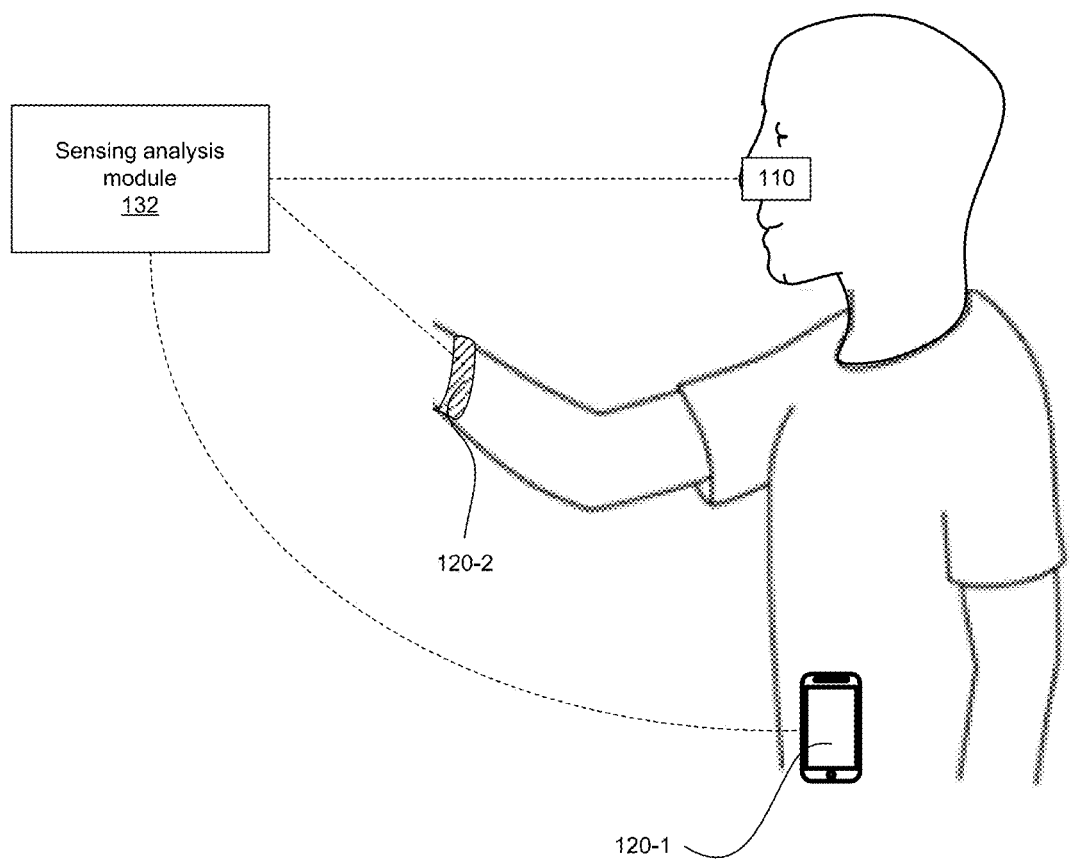
FIG. 3 shows a schematic of a user utilizing an air filtration and sensing device.

FIG. 3 illustrates the communication between a wearable air filtration and sensing device, one or more user devices, and a sensing analysis module, in accordance with some embodiments. The wearable device 110 may be worn within the user's nasal passages or over the user's mouth and/or nose, as described herein. The wearable device may be communicatively coupled to user devices 120-1 and/or 120-2. The user device 120-1 may be a mobile device carried by the user, and may include one or more sensors such as cameras, microphones, accelerometers, gyroscopes, compasses, GPS, etc. The user device 120-2 may be a wrist-wearable device such as a smartwatch or wristband, which may include one or more sensors for measuring body temperature, heart rate, motion of the user, etc. The wearable device 110 and user devices 120-1 and/or 120-2 may be communicatively coupled to the sensing analysis module 132. The sensing analysis module may be an app or other program held in memory on the mobile device and/or wrist-wearable device. The sensing analysis module may be peripheral hardware components communicatively coupled to the mobile device and/or wrist-wearable device. The sensing analysis module may be configured to receive input data from the various devices 110, 120-1 and 120-2, as described elsewhere herein.

Figure 4A:
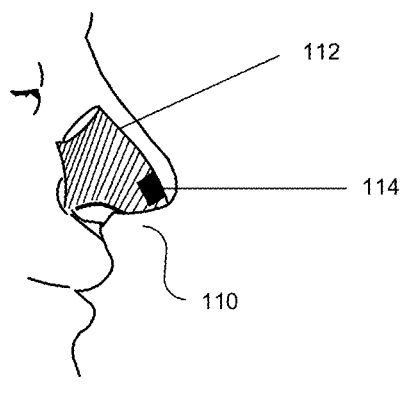
FIG. 4A shows an air filtration and sensing device worn inside of a user's nasal passage.

FIG. 4A shows an air filtration and sensing device worn inside of a user's nasal passage. The air filtration and sensing device 110 may comprise an intranasal device worn inside the user's nasal passages. The intranasal device may be worn entirely within the user's nasal passages. The intranasal device may be worn partially within the user's nasal passages. The filtration module 112 may intercept natural airflow taken into the user's nostrils during inhalation. The sensing module 114 may intercept natural airflow expelled from the user's nostrils during exhalation.

Figure 4B:
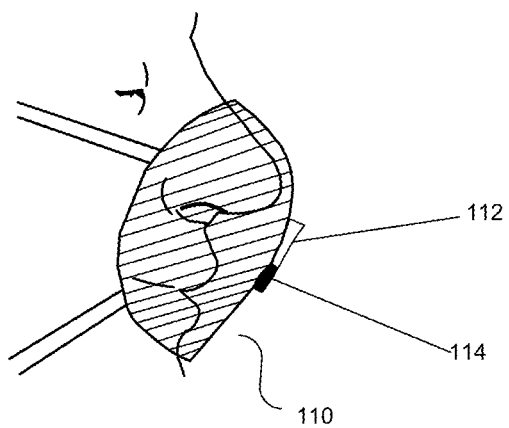
FIG. 4B shows an air filtration and sensing device worn over a user's nose and mouth.

FIG. 4B shows an air filtration and sensing device worn over a user's nose and mouth. Unlike FIG. 4A, the air filtrations and sensing device 110 in FIG. 4B may comprise a face mask device worn over the user's nose and mouth. The filtration module 112 may intercept natural airflow taken into the user's nostrils or mouth during inhalation. The sensing module 114 may intercept natural airflow expelled from the user's nostrils or mouth during exhalation.

Figure 5A:
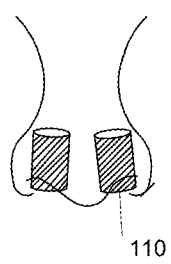
FIG. 5A shows a front view of an intranasal air filtration and sensing device worn entirely within a user's nasal passage.
Figure 5B:
FIG. 5B shows a side view of an intranasal air filtration and sensing device worn entirely within a user's nasal passage.
Figure 5C:
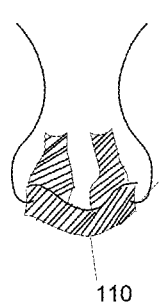
FIG. 5C shows a front view of an intranasal air filtration and sensing device worn partially within a user's nasal passage.
Figure 5D:
FIG. 5D shows a side view of an intranasal air filtration and sensing device worn partially within a user's nasal passage.

FIG. 5A shows a front view of an intranasal air filtration and sensing device that is worn substantially within a user's nasal passage. The intranasal device 110-1 may be worn such that a certain volume of the device (e.g., greater than 90%) is located within a user's nasal passage. FIG. 5B shows a side view of the intranasal air filtration and sensing device of FIG. 5A. FIG. 5C shows a front view of an intranasal air filtration and sensing device worn partially within a user's nasal passage. The intranasal device 110-2 may be worn such that greater than 10%, greater than 20%, greater than 30%, greater than 40%, greater than 50%, greater than 60%, greater than 70%, or greater than 80% of the volume of the device is located within a user's nasal passage. FIG. 5D shows a side view of the intranasal air filtration and sensing device of FIG. 5C.

Figure 6A:
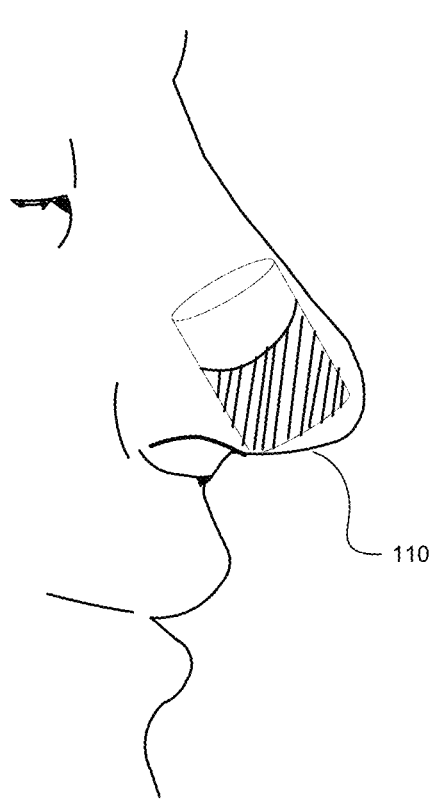
FIGS. 6A and 6B show a schematic of a cartridge-based intranasal air filtration and sensing device.
Figure 6B:
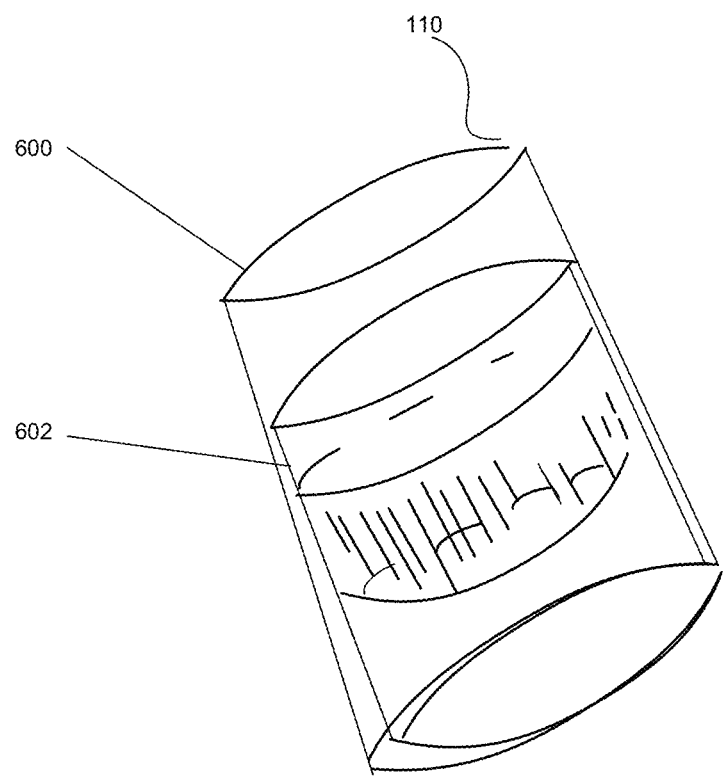

FIG. 6A shows a schematic of a cartridge-based intranasal air filtration and sensing device 110 worn within a user's nasal passageway. FIG. 6B shows a magnified view of the device 110 of FIG. 6A. The intranasal air filtration and sensing device may comprise an intranasal filtration module 112, as described herein. The intranasal filtration module may comprise a cartridge holder 600 and a filter cartridge 602. The cartridge holder may be configured to receive and couple to the filter cartridge, in order to hold the filter cartridge in place within the intranasal filtration in module. The cartridge holder may be configured to reversibly couple to the filter cartridge in order to allow different filter cartridges to be utilized at different moments in time. The cartridge holder may be configured to allow the filter cartridge to snap in and out of the cartridge holder.

In some cases, the cartridge filter may be configured to be interchanged. The cartridge filter may be mounted onto the cartridge holder using a quick release mechanism. The cartridge filter may be configured to be interchanged and/or mounted onto the cartridge holder without using tools. The cartridge filter and/or cartridge holder may comprise security features, such as mechanical and/or electrical keys or interlocks.

The use of a cartridge-based filtration element may allow the useful performance lifetime of the filtration module to be extended. Air filters may clog as pollutants accumulate, requiring the filtration elements to be periodically replaced. The use of an easy-to-replace cartridge format may address the need to replace filter elements. The use of a cartridge format may have the additional advantage of allowing a filter with a varying and potentially highly complex internal composition to be easily snapped in and out of the cartridge holder as a single monolithic object.

The use of a cartridge-based filtration module may also allow the filtration element to be customized for a given user's needs or preferences. For instance, different filtration properties may be required for different users, such as a physician, a woodworker exposed to saw dust, an expectant mother in Beijing, an asthmatic, a person recovering from a medical intervention, and a person with sleep apnea. In general, different users will have different preferences, ranging from zero filtration (no cartridge) to maximum filtration. The physician may seek to maximize protection to airborne viruses and bacteria. The woodworker generating wood dust may prefer filter cartridges that remove dust and large particulate matter. An expectant mother in Beijing may seek filter cartridges that best protect her and her fetus from PM2.5 particulate matter and carbon monoxide. The athlete may prefer a filter cartridge that provides the highest possible airflow through the filtration element. A person recovering from a medical intervention at home, having a medical condition, or wishing to collect data about their breathing may desire zero filtration, using the device to measure, monitor, and report respiratory rate, volume, and other vital signs. Similarly, a person suffering from sleep apnea may utilize the device solely for the purpose of measuring, monitoring, and reporting information about their breathing during sleep. In some cases, a user may utilize the sensing module to detect other exhaled compounds, such as metabolic end-products or other volatile organic compounds. In some cases, a user may wish to utilize the sensing module to detect changes in exhaled compounds which may relate to their participation in a medical treatment program, such as the use of therapeutic medications. The use of a removable and replaceable cartridge-based filtration module may allow each of these users to utilize a filtration cartridge having an internal composition customized for their particular needs, which may change over time or be determined by their location, activity, and health status.

Figures 7A, 7B:
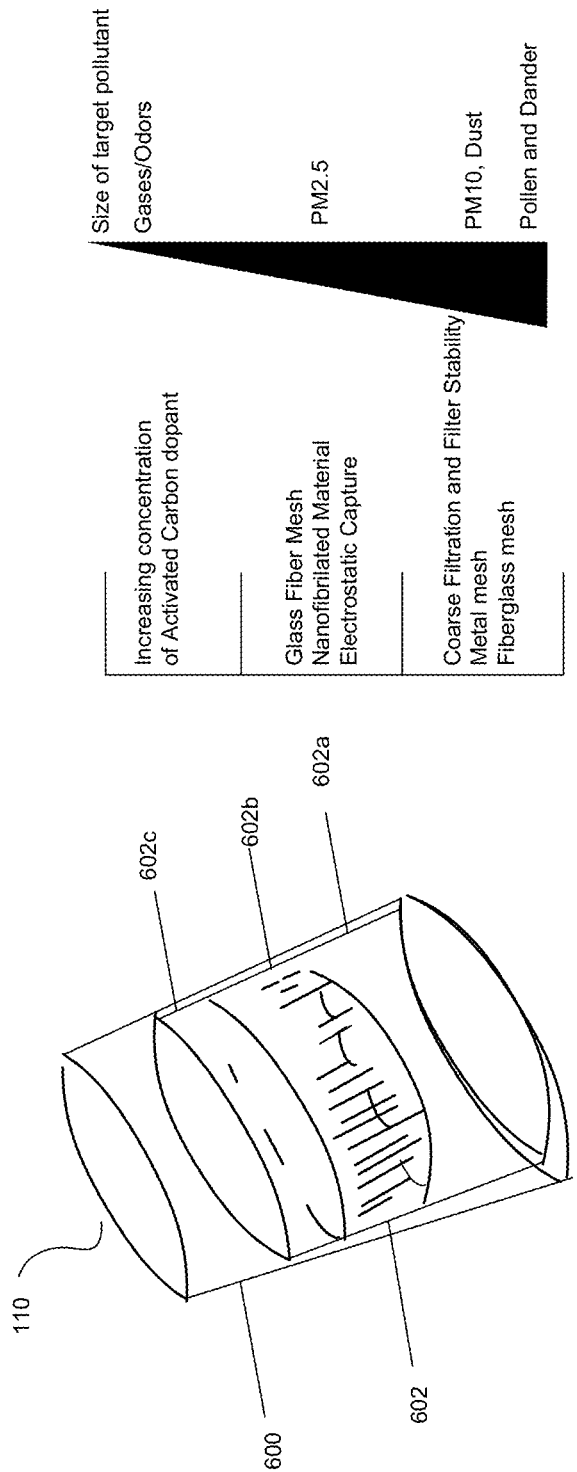
FIGS. 7A and 7B show a schematic of a cartridge-based intranasal air filtration device comprising a plurality of filtration layers.

FIG. 7A shows a schematic of a cartridge-based intranasal air filtration device comprising a plurality of filtration layers. The intranasal air filtration and sensing device may comprise an intranasal filtration module 112, as described herein. The intranasal filtration module may comprise a cartridge holder 600 and a filter cartridge 602. The filter cartridge may comprise one or more layers. The filter cartridge may comprise a first layer 602a, a second layer 602b, and a third layer 602c. The filter cartridge may comprise 1, 2, 3, 4, 5, 6, 7, 8, 9, 10, or more than 10 layers.

The layers may contain a plurality of components in varying amounts and thicknesses. The overall composition of the cartridges may be formulated to address specific pollutants, pollutant levels, and user preferences. The internal composition and structure of the filtration elements determines their overall filtration characteristics and associated parameters, such as the inhalation resistance, exhalation resistance, moisture and heat experienced by the user when wearing the device.

Referring to FIG. 7B, the layers may be arranged in order of decreasing size of the target pollutant, with the largest pollutants being excluded at the earliest possible location within the filter. For instance, the first layer 602a may comprise a coarse filtration element, such as a metal mesh or a fiberglass mesh, to filter relatively large pollutants such as pollen, dander, PM10, or dust. The second layer 602b may comprise a less coarse filtration element, such as a glass fiber mesh, a nanofibrilated material, or an electrostatic capture device, to filter smaller pollutants such as PM2.5. The third layer 602c may comprise a fine filtration element, such as an activated carbon dopant added to a substrate, to filter gasses such as CO, or $NO_x$. The third layer may be configured to filter gasses and other pollutants with activated carbon whose pore volume distribution (and therefore the relative fractions of micro-, meso-, and macro-pores) has been matched to the expected, predicted, or known chemical characteristics. Accordingly, the layers may comprise a coarse filtration element, a less coarse filtration element, or a fine filtration element. In some embodiments, elements with varying degrees of filtration capabilities can be fabricated into a single layer, with increasing and/or decreasing levels of granularity.

FIG. 8 shows a flowchart of a method of providing a user with a customized air filtration device. The method 800 may comprise providing various input data (e.g., location, season, crowd-sourced data, user health information, etc.) to a sensing analysis module (step 805). Next, the sensing analysis module can determine an optimal filter for the user based on the input data (step 850). The filter can be fabricated for the user, and subsequently shipped to the user, for example by a third party entity (manufacturer).

The input data may include a user's location 810. Providing the location may allow information about the locality to be utilized in determining an optimal filter for the user. For instance, measurements of the concentrations of a variety of air pollutants (such as plant pollen, CO, NOx, PM2.5, PM10, or other pollutants) from fixed environmental sensors at the location may be utilized to determine which filtration layers to include in a filtration cartridge to be utilized by the user.

The input data may include information about the current season 820. Providing information about the season (e.g., which season of the year, beginning of the season, mid or end of season) may allow temporal information to be utilized in determining an optimal filter for the user. For instance, measurements of the concentrations of a variety of air pollutants (such as plant pollen, CO, NOx, PM2.5, PM10, or other pollutants) from fixed environmental sensors at the location during different seasons may be utilized to determine which filtration layers to include in a filtration cartridge to be utilized by the user. In this manner, different optimal filters can be utilized for different seasons. For instance, an optimal filter for spring may include layers designed to filter pollen or other spring-time allergens, while an optimal filter for winter may not require these layers.

The input data may also include crowd-sourced information 830. The crowd-sourced information may comprise information relevant to determining a user's exposure to air pollutants. For instance, the crowd-source information may comprise information about current air pollutant levels at one or more locations, predicted future air pollutant levels at one or more locations, or any other information relevant to determining the user's exposure to air pollutants. The crowd-sourced information may comprise information obtained from websites or applications, such as newsfeeds, social media websites or applications. The crowd-sourced information may comprise information obtained from other devices utilized by other users. The crowd-sourced information may comprise information obtained from local or network newscasts. The crowd-sourced information may comprise information obtained from sources that track air pollutant levels, such as the National Weather Service (NWS) and/or National Oceanic and Atmospheric Administration (NOAA). Additionally or alternatively, the crowd-sourced information may comprise other sources of information such as health-related web sites (such as patientslikeme) and search engines, which can provide information about trending web searches (such as the number of people searching for 'flu-like symptoms' in a particular geographic location).

The input data may also include user health information 840. The user health information can be used to determine an optimal filter for the user. For instance, if the user has an allergy to a particular substance (such as pollen) in the atmosphere, such information may be utilized to include a filtration layer to filter that allergen. Likewise, if the user has sleep apnea and wishes to monitor and record his or her breathing at night, the user may wish to forgo any kind of filtration and use the device only for health sensing and monitoring.

In step 850, an optimal filter for the user is determined by the sensing analysis module. The optimal filter may be determined by considering one or more pieces of the input data provided in step 805. The optimal filter may be determined from additional pieces of information, such as a user's personal preferences, as described herein.

The filter can be fabricated using any fabrication methods. For instance, the filter may be fabricated utilizing laser fabrication methods, such as laser cutting, laser perforation, and/or laser spot welding. The filter may be fabricated utilizing additive manufacturing techniques, such as 3D printing. The filter may be fabricated utilizing any rapid fabrication methods as are known to one skilled in the art.

A person of ordinary skill in the art will recognize many variations, alterations and adaptations based on the disclosure provided herein. For example, additional steps may be added as appropriate. Some of the steps may comprise sub-steps. Some of the steps may be automated (e.g., autonomous pollutant and/or environmental sensing), whereas some of the steps may be manual (e.g., requiring manual input or responses from a user). The systems and methods as described herein may comprise one or more instructions to perform at least a portion of one or more steps of method 800.

The capability to manufacture a practically unlimited diversity of chemically and physically distinct filter cartridges may result in better health outcomes and better protection of people from air pollutants. Additionally, rapid fabrication technologies may be combined with an integrated sensing, fluid dynamics, and analytics infrastructure that allows geographically-, temporally-, and user-optimized filter elements to be rapidly formulated.

Personalized filter formulation and rapid manufacturing may only partially address a user's filtration needs. For instance, an athlete in Beijing in the summer may seek a different level of protection compared to a pregnant woman in the same location. The athlete may wish to minimize the filtration module's resistance to respiration, a filter element consisting solely of a porous metal mesh with a mesh size of 3 microns. By contrast, the expectant woman may wish to maximize protection from all known pollutants, encompassing dust and gasses such as carbon monoxide, pointing to a much more complex multi-element filter with activated carbon, metal meshes, and woven glass fibers. Such a filter might be optimal for the expectant woman, but have an intolerably high resistance to respiration for an athlete.

Therefore, rapid filter formulation and rapid filter manufacturing may be combined with a user interface software that allows the user to indicate personal choices about their current preferences regarding their preferred tradeoff between comfort and desired protection levels. For instance, the software may allow the user to drag a slider from left (red) to right (green) to indicate their protection preference. The user interface element may be labeled with words that clarify the choice the user is making concerning the ease of breathing versus protection. For instance, the software may include such wording as 'best protection' on one end of the slider element and 'easiest breathing' on the other.

The software may use real-time sensor data from a miniaturized air pollution sensor worn by a user to suggest changes in personal habits or changes in filter cartridge composition to reduce exposure. The software back-end may track exposure and activity to predict when a user will require a new shipment of filter cartridges, and will ask and/or remind the user to reorder filter cartridges.

In some implementations, a sensor within or near the filtration system may process sensing data locally and/or transmit the sensing data to the sensing analysis module. The sensing analysis module can provide feedback to the user and allow the user to monitor pollution levels and the performance of their filter, based on the sensing data. Relevant events and changes may be signaled to the user via a buzzer, sound, or light signals.

Data from a local sensor and data from remote and/or crowd sensors may be integrated by a central computer (e.g., implemented as a sensing analysis module) allowing information to be provided to the user, such as pollution-minimizing walking/traffic routing information and local pollution levels. Pollution information and associated data (such as an optimized exposure-minimizing route) may be provided to the user, allowing the user to change their actions and choices, such as the type of filter they wish to use in their filtration system.

For instance, an athlete with a "high-flow" filter cartridge may wish to be warned if the local ozone levels exceed a preset level, allowing them to stop their exercise or otherwise respond to that environmental change, such as by snapping a different type of filter cartridge into a flexible carrier structure that sits stably in their nose.

The need to select between better filtration and increased airflow may be partially mitigated by incorporating additional elements to increase the airflow while maintaining a high level of filtration performance. For instance, the air filtration and sensing device may comprise a filtration element utilizing micro- or nano-fibrous elements, a dilation structure to open the nasal passage, or a filter cartridge that changes position within the nasal passages during inhalation and exhalation.

Figures 9A, 9B:
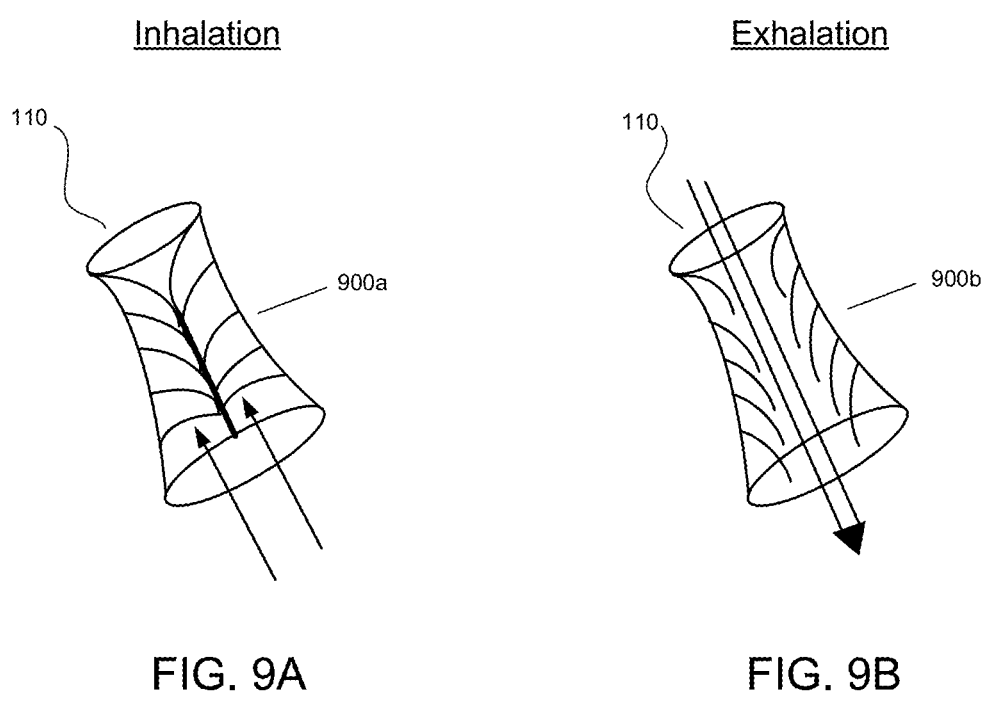
FIG. 9A shows a schematic of a cartridge-based intranasal air filtration device comprising a plurality of filtration elements, during a period in which a user is inhaling.
FIG. 9B shows a schematic of a cartridge-based intranasal air filtration device comprising a plurality of filtration elements, during a period in which a user is exhaling.

FIG. 9A shows a schematic of a cartridge-based intranasal air filtration device comprising a plurality of filtration elements, during a period in which a user is inhaling. The filtration module 112 may comprise a plurality of fibrous elements in a first configuration 900a during inhalation. The filtration elements may comprise micro-fibrous elements. The filtration elements may comprise nano-fibrous elements. The filtration elements may comprise a mesh, such as a fine metal mesh. The filtration elements may comprise one or more membranes. The filtration elements may comprise one or more granulated chemicals. The filtration elements may be shaped like the valves of the human heart. During inhalation, the filtration elements may be in a "closed" configuration and arranged in a tight grouping with little space located between adjacent elements. In this manner, the filtration elements may provide filtration of air during inhalation.

FIG. 9B shows a schematic of a cartridge-based intranasal air filtration device comprising a plurality of filtration elements, during a period in which a user is exhaling. The filtration module 112 may comprise a plurality of filtration elements in a second configuration 900b during exhalation. During inhalation, the filtration elements may be in an "open" configuration and arranged in a loose grouping with little space located between adjacent elements. In the manner, the filtration elements may have a reduced resistance to exhalation, when extensive filtration of the air may not be necessary.

Figure 10A:
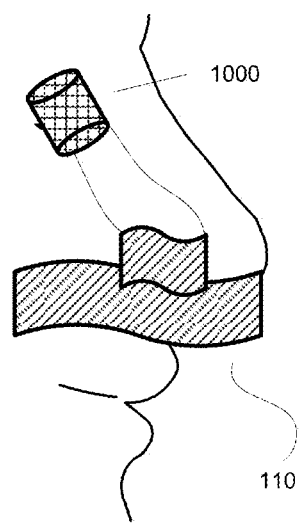
FIG. 10A shows a schematic of a cartridge-based intranasal air filtration and sensing device comprising a dilation structure to open the nasal passage for increased airflow.

FIG. 10A shows a schematic of a cartridge-based intranasal air filtration and sensing device comprising a dilation structure to open the nasal passage for increased airflow. The filtration module 112 may comprise a dilation structure 1000 that dilates natural constrictions that are located deep within the nasal cavity and that naturally increase the nasal passages' resistance to airflow. The dilation structure may dilate any structure within the nose that would otherwise restrict the flow of air through the nasal passages. For instance, the dilation structure may dilate the aperture defined by the nasal septum and the base of the Inferior Turbinate, which may be a critical choke point for air in the nasal passages. This aperture can have a lateral dimension of less than 3 mm, creating a high drag choke-point for the flowing air.

Figure 10B:
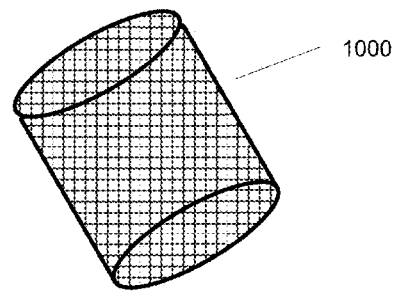
FIG. 10B shows a schematic of a dilation structure to open the nasal passage for increased airflow.

FIG. 10B shows a magnified view of the dilation structure of FIG. 10A. The dilation structure may comprise a flexible elastic mesh. The flexible elastic mesh may be located at least 1 mm, at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, or at least 15 mm deep within the nasal cavity as measured from the base of the nostril. The flexible elastic mesh may dilate this natural construction, yielding a reduction of air resistance.

Figure 11A:
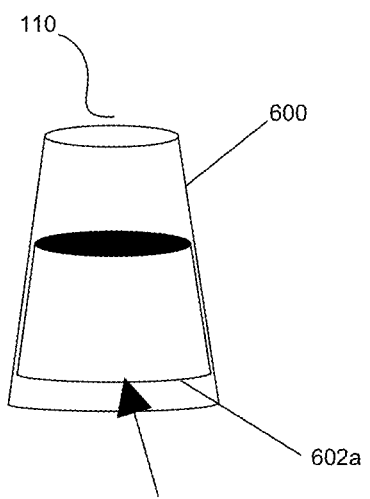
FIG. 11A shows a cartridge-based air filtration device in a position allowing increased filtration and reduced airflow during a period in which a user is inhaling.

FIG. 11A shows a cartridge-based air filtration device in a position allowing increased filtration and reduced airflow during a period in which a user is inhaling. The filtration module 112 may comprise a cartridge holder 600 and a cartridge 602, as described herein. The cartridge may be movable, such that its position within the cartridge holder may change over time depending on which part of the breathing cycle the user is undergoing. During inhalation, the cartridge may be in a first position 602a in which the cartridge is located with relatively little space between the cartridge holder and the cartridge. The relatively small amount of space between the cartridge holder and the cartridge may force air through the cartridge during inhalation, allowing filtration of the incoming air.

Figure 11B:
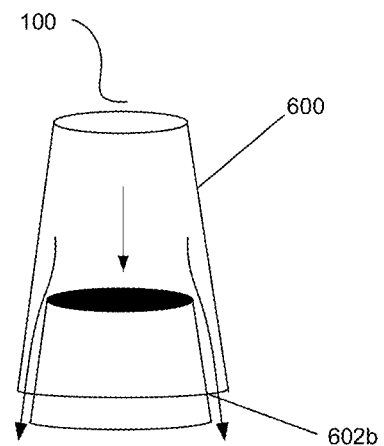
FIG. 11B shows a cartridge-based air filtration device in a position allowing reduced filtration and increased airflow during a period in which a user is exhaling.

FIG. 11B shows a cartridge-based air filtration device in a position allowing reduced filtration and increased airflow during a period in which a user is exhaling. The filtration module 112 may comprise a cartridge holder 600 and a cartridge 602, as described herein. During exhalation, the cartridge may be in a second position 602b in which the cartridge is located with a relatively large amount of space between the cartridge holder and the cartridge. The relatively large amount of space between the cartridge holder and the cartridge may allow air to pass around the cartridge, thereby decreasing the resistance to airflow.

The provision of alternative air exit paths may have other benefits beyond making it easier to exhale. For example, the exhaled air may be moist and carry this moisture into the filter, where it can accumulate and potentially degrade filtration. By providing alternative exit paths for the exhaled air, the air may be able to leave the filtration system without needing to pass through the filter element, thereby extending the lifetime and/or performance of the filtration module.

The filtration module may include a shell allowing customization of the fit within a user's nasal passages. The shell may be made of a plastic material. The shell may be fabricated with rapid fabrication technologies such as 3D printing. Slight imperfections between the plastic shell and the nasal anatomy may be filled with materials that allow the final shape to be molded after the device has been provided to the user. For instance, the gap-filling material may consist of a thermoplastic polymer. The thermoplastic polymer may have a melting point of between 45 and 85 degrees Celsius, 45 and 80 degrees Celsius, 50 and 75 degrees Celsius, 50 and 70 degrees Celsius, 55 and 65 degrees Celsius, or 55 and 60 degrees Celsius. The melting point may be chosen to be compatible with the thermosensitivity of tissues with the human nose, which may sharply limit the temperature of a thermoplastic material that can be inserted into the human nose without causing discomfort. The thermoplastic material may contain a temperature sensitive dye, so that the user can confidently and reliably determine the correct temperature of the thermoplastic material to maximize shaping capability and comfort while forming the material and waiting for it to set.

The filtration module may include one or more of the air resistance reduction strategies described herein along with a filter element. The filter element may comprise a low-resistance nano-structured or nano-fibrilated polymer mesh that can provide good particle filtration performance with reduced air resistance. For instance, the materials may allow pressure drops that are lower by at least a factor of two compared to conventional air filter materials.

The sensing module may comprise one or more sensor elements. The sensor elements may comprise one or more air pollution sensors capable of detecting one or more air pollutants such as gasses (e.g. CO, NOx, ozone, or sulfur-containing compounds), particulate matter (e.g. soot, dust, PM2.5, or PM10), or biological particles (e.g. pollen, bacteria, or viruses). The air pollution sensors may comprise optical sensors based on the reflection, transmission, absorption, or scattering or light. The air pollution sensors may comprise optoelectronic sensors. The air pollution sensors may comprise chemical reactivity sensors. The air pollution sensors may comprise mass sensors based on changes in vibrational characteristics.

In addition to air pollution sensors, the sensing module may comprise one or more complementary sensors providing complementary information. The complementary sensors may comprise one or more global positioning system (GPS) sensors for detecting a location of the air filtration and sensing device. The complementary sensors may comprise one or more inertial sensors such as accelerometers or gyroscopes for detecting an orientation of the air filtration and sensing device. The complementary sensors may comprise one or more altitude sensors such as a barometer for measuring an altitude of the air filtration and sensing device. The complementary sensors may comprise one or more external temperature, humidity, air pressure, or wind speed sensors for measuring a temperature, humidity, air pressure, or wind speed, respectively, in the environment of the air filtration and sensing device. The complementary sensors may comprise one or more heart rate monitors for measuring a heart rate of a user. The complementary sensors may comprise one or more skin temperature sensors for detecting a skin temperature of a user. The complementary sensors may comprise one or more galvanic skin response sensors for determining electrical characteristics of the skin of a user. The complementary sensors may comprise one or more blood oxygen saturation sensors. The complementary sensors may comprise one or more metabolic sensors for measuring metabolic function of a user. The complementary sensors may comprise one or more capacitive sensors responding to a touch of a user. In some cases, the sensors may comprise microelectromechanical systems (MEMS) or nanoelectromechanical systems (NEMS) sensors. In some cases, the MEMS or NEMS sensors can be configured to be removable from the sensing module. For instance, the sensing module can be configured to be allow MEMS or NEMS sensors to be replaced with other sensors based on user or environmental circumstances.

Figure 12:
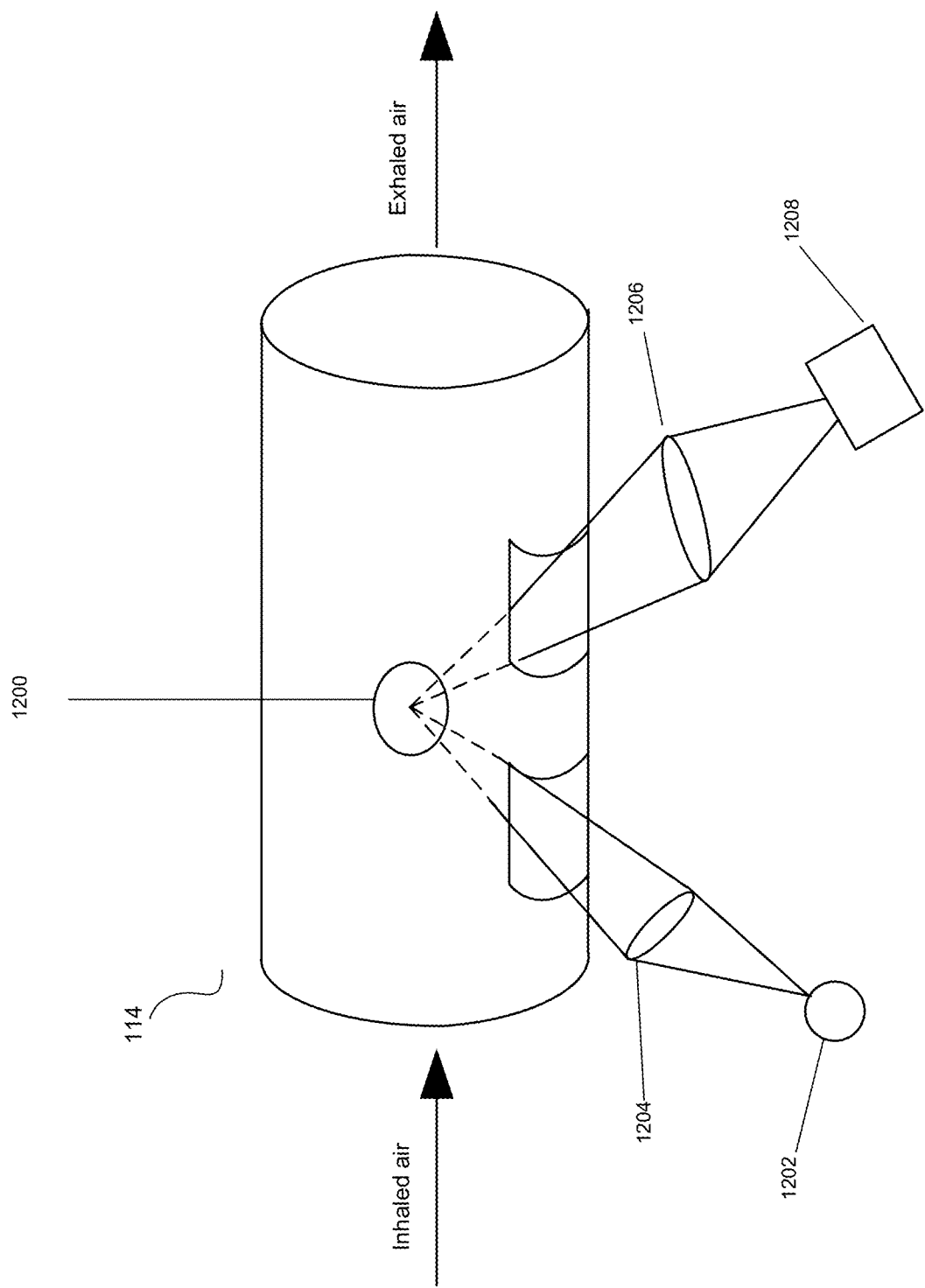
FIG. 12 shows a schematic for an air sensing device utilizing an optical detection scheme.

FIG. 12 shows a schematic of an air sensing device utilizing an optical detection scheme. The sensing module 114 may comprise an optical detector utilizing scattering of light to detect one or more air pollutants. The optical detector may comprise a light source 1202, collimating optics 1204, light collecting optics 1206, and a detector 1208. The light source may comprise a broadband light source such as a light emitting diode (LED). The light source may comprise a semi-monochromatic light source such as a laser. The light source may comprise a continuous wave laser or a pulsed laser. The light source may comprise a gas (e.g. carbon dioxide or helium-nitrogen) laser, a dye laser, a solid-state laser (e.g. a Nd:YAG laser), a fiber laser (e.g. a rare-earth doped fiber laser), a semiconductor laser (e.g. a vertical cavity surface emitting laser), or any other laser as is known to one having skill in the art. The light source may comprise multiple light sources.

The light source directs light to the collimating optics. The collimating optics direct light from the light source to a pollutant 1200 under investigation by the optical sensor. The collimating optics may collimate the light as it is passed to the pollutant under investigation by the optical sensor. The collimating optics may comprise one or more lenses. The collimating optics may comprise one or more microlenses. Upon interaction with the pollutant, light is scattered toward the light collection optics.

The light collection optics direct light scattered from the pollutant to the detector. The light collection optics may comprise focusing optics which focus the scattered light as it is passed to the detector. The light collection optics may comprise one or more lenses. The light collection optics may comprise one or more microlenses. The light collection optics may comprise one or more ball lenses. The light collection optics may comprise one or more mirrors. The light collection optics may comprise one or more micromirrors. The light collection optics may comprise one or more parabolic mirrors. The light collection optics may comprise one or more parabolic concentrators. The light collection optics may comprise one or more compound parabolic concentrators.

The detector registers an optical signal that may be indicative of the presence of a pollutant. The detector may comprise one or more photodiodes, one or more avalanche photodiodes, one or more charge-coupled device (CCD) cameras, or one or more complementary metal oxide semiconductor (CMOS) cameras. The detector may comprise any other detector as is known to one having skill in the art. The detector may be coupled to one or more lock-in amplifiers allowing lock-in detection of the optical signal.

The optical detector may comprise one or more additional optical elements that may minimize the aspect ratio or size of the optical sensor by folding the optical path into a more compact space. For instance, the additional optical elements may allow the optical path to be converted into a U-shaped optical path.

Figure 13B:
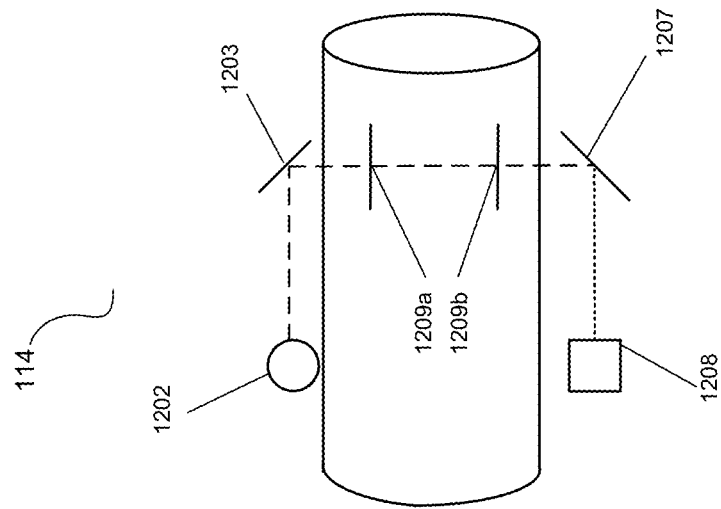
FIG. 13B shows a schematic for an air sensing device utilizing an optical detection scheme with a reduced optical path length comprising one or more polarizing elements.
Figure 13A:
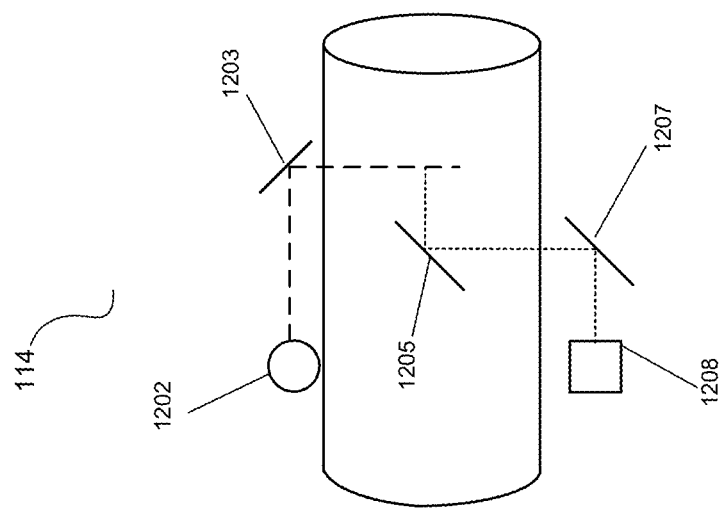
FIG. 13A shows a schematic for an air sensing device utilizing an optical detection scheme with a reduced optical path length comprising one or more mirrors.

FIG. 13A shows a schematic for an air sensing device utilizing an optical detection scheme with a reduced optical path length comprising one or more mirrors. The optical sensor 114 described herein may comprise the light source 1202, collimating optics 1204, light collection optics 1206, and detector 1208. In addition, the optical sensor may comprise mirrors 1203, 1205, and 1207. The mirrors may produce a U-shaped optical path of light through the optical sensor. The mirrors may comprise micromirrors.

FIG. 13B shows a schematic for an air sensing device utilizing an optical detection scheme with a reduced optical path length comprising one or more polarizing elements. The optical sensor 114 described herein may comprise the light source 1202, collimating optics 1204, light collection optics 1206, and detector 1208. In addition, the optical sensor may comprise one or more mirrors 1203 and 1207, and one or more polarizing elements 1209a and 1209b. The mirrors may comprise micromirrors. The polarizing elements may comprise two polarizing elements. The polarizing elements may comprise a pair of crossed polarizers. The crossed polarizers may minimize the entry of light that has not been scattered by a pollutant into the detector.

The sensing module may comprise one or more air pollution sensors utilizing a non-optical detection principle. For instance, the sensing module may comprise air pollution detectors based on quartz crystal microbalances or other resonators for mass measurement. The sensing module may comprise air pollution detectors that are placed into contact with air that naturally moves through a human airway due to respiration. The sensors may be arranged in a variety of geometries within the channel or on the surface of the channel such as in a ring architecture or a staggered spiral, to avoid sensor-to-sensor interference. Although the figure shows the sensor(s) placed within a cylindrical channel, the specific shape of the structure over which (or through which) the air moves can vary widely (e.g. a flat surface, a cylindrical channel, or an otherwise curved surface).

Figure 14A:
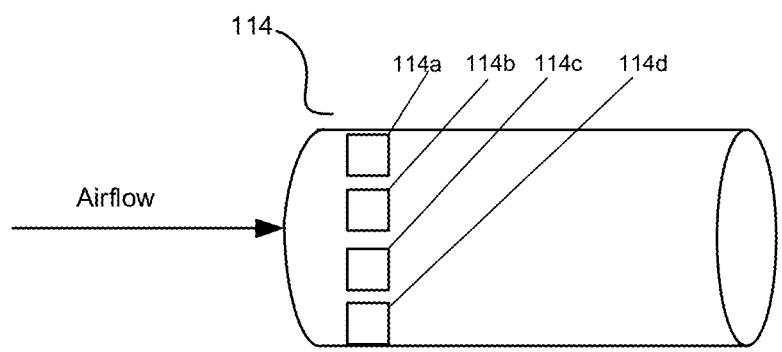
FIG. 14A shows a schematic for an air sensing device comprising a plurality of sensing elements arranged in a linear manner.

FIG. 14A shows a schematic for an air pollution sensing device comprising a plurality of sensing elements arranged in a linear manner. The sensing module 114 may comprise one or more sensors 114a, 114b, 114c, and 114d arranged in a linear manner across a dimension of the sensing module.

Figure 14B:
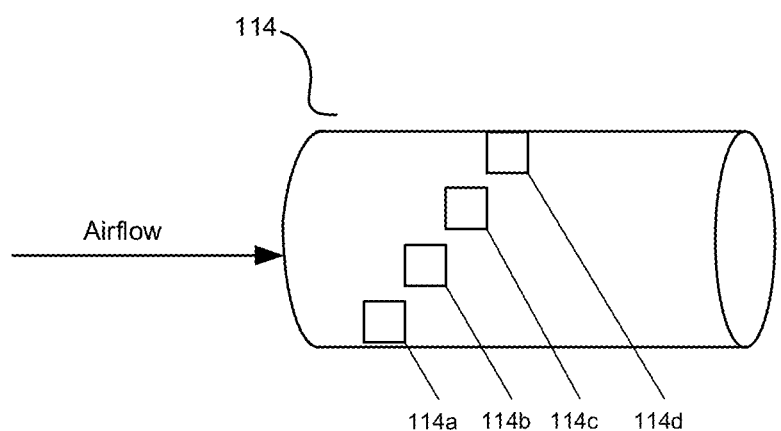
FIG. 14B shows a schematic for an air sensing device comprising a plurality of sensing elements arranged in a staggered manner.

FIG. 14B shows a schematic for an air pollution sensing device comprising a plurality of sensing elements arranged in a staggered manner. The sensing module 114 may comprise one or more sensors 114a, 114b, 114c, and 114d arranged in a staggered manner across the sensing module. For instance, the sensors may be arranged in a spiral or in a ring. The use of a staggered geometry may minimize interference between the sensors. For example, a chemical sensor that locally impedes airflow could impair the performance of a pressure sensor located downstream from the chemical sensor. Likewise, a heated MEMS sensor could bias the performance of a temperature sensor located downstream from the heated MEMS sensor. These forms of sensor interference may be reduced by staggering the sensors in a spiral path relative to the airflow.

The sensing module may contain more than one sensor, such that other parameters of the moving air (e.g. pressure, velocity, temperature, and humidity) are sampled. Measurement of these parameters may facilitate the accurate calibration and normalization of gas concentration, air quality, and/or particulate matter.

For instance, measurement of the velocity of the air flowing through a channel of defined diameter may allow the flux of air into and out of the body to be estimated. This in turn may allow the exposure to an air pollutant (e.g. particulate matter) to be calculated. Such a calculation may involve the signal from an air pollution sensor, the signal from an air velocity sensor, and the cross-sectional area of the channel through which the air is entering the human body. For example, a measured air velocity of 180 cm/s may be multiplied by the cross-sectional area of a cylindrical channel with a radius of 1 cm to yield a volume of 570 cm$^3$ of air moving through this channel per second. A particulate matter sensor may measure a concentration of 0.6 mg/m$^3$. This concentration may be multiplied by the volumetric flow rate to conclude that the wearer has inhaled 0.0003 mg of particulate matter per second. The instantaneous particular matter exposure may be integrated to determine a total exposure of the user to particulate matter during a particular period of time.

The air velocity may be determined from a measurement of the air pressure using a pressure sensor. The measurement of the air pressure inside a channel of a defined diameter may allow the flux of air into and out of the body to be estimated utilizing Bernoulli's equation. The addition of a temperature reading from a temperature sensor may be used to correct the raw pressure signal and obtain a corrected air velocity.

The sensing module may be configured to operate with reduced power consumption and to operate in sync with a user's breathing cycle. The sensing module may be coupled to hardware or software that utilizes predictive algorithms to monitor airway pressure and flow in a user's nasal passages. Such respiratory information may be utilized to adaptively gate the timing of gas sensing windows to allow sampling by one or more air pollution sensors only when a user is inhaling or exhaling.

The sensing module may be configured to use information from a pressure sensor to predict when the next exhalation cycle will be and to optimally gate the gas sensing window based on the prediction. For example, an energy- and information-efficient sampling procedure may be to gate a nondispersive infrared (NDIR) sensing cycle ~600 ms after onset of exhalation. As the wearer changes their respiratory rate, the sensing module may change the gating such that the gas sensing event always occurs at the same time relative to onset of exhalation.

The sensing module may use information from a pressure sensor to anticipate when the next exhalation cycle will be, and uses that prediction to perform a pair of measurements, one occurring during inhalation, and the other occurring during exhalation. By comparing these two numbers, and performing a differential measurement that is optimally and adaptively synchronized to human breathing, the sensing module may be able to provide robust estimates of the exhaled gas composition regardless of the potentially varying gas composition of the inhaled air.

The sensing module may use information from a pressure sensor to anticipate when the next exhalation cycle will be, and use that prediction to sample the exhaled breath at different delay timings relative to the onset of exhalation. As a person exhales, the air contained in the lung is forced out of the body, with different air volumes coming from different regions within the human airway. For example, air leaving the human body about 100 ms after onset of exhalation may come mostly from the nasal cavity and upper respiratory tract. By contrast, air leaving the nose about 800 ms after onset of exhalation may come mostly from the nasal cavity and lower respiratory track. If the sensing module monitors respiration via a pressure sensor, the sensing module may be able to use that information to obtain multiple samples of the exhaled air, and therefore differentially probe air coming from different regions of the human airways.

The sensing module may be partially or entirely powered by a power generating module capable of converting mechanical energy from breathing into electrical energy. The power generating module may comprise one or more power generating elements configured to fit within or near airways of the human body. The power generating elements may intercept some or all of the air moving through the human airway. The power generating elements may be configured to fit within the nasal cavity.

Figure 15A:
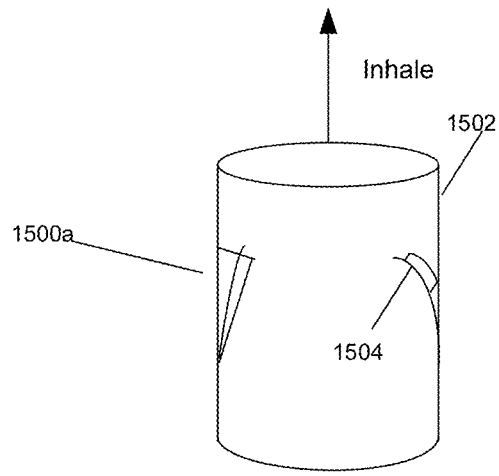
FIG. 15A shows a schematic for a device capable of converting energy from breathing to electrical energy comprising a piezoelectric element attached to flexible vanes of a one-way valve, during a period in which a user is inhaling.

FIG. 15A shows a schematic for a device capable of converting energy from breathing to electrical energy comprising a piezoelectric element attached to flexible vanes 1504 of a one-way valve 1502, during a period in which a user is inhaling. The power generating module may comprise one or more piezoelectric elements bonded to the flexible vanes of a one-way air valve. During inhalation, the vanes may be in a first configuration 1500a. In this first configuration, the vanes may be configured such that the piezoelectric elements are in a stressed configuration and produce a flow of electric current. The passage of air during inhalation may maintain the vanes in the first configuration, allowing an electric current to be generated as long as a user is inhaling.

Figure 15C:
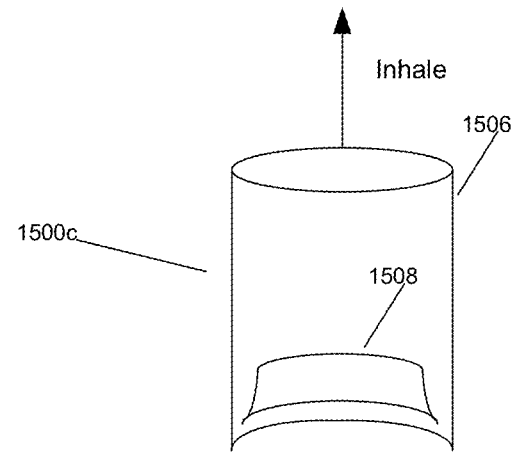
FIG. 15C shows a schematic for a device capable of converting energy from breathing to electrical energy comprising a piezoelectric element attached to the surface of an air-carrying tube, during a period in which a user is inhaling.
Figure 15B:
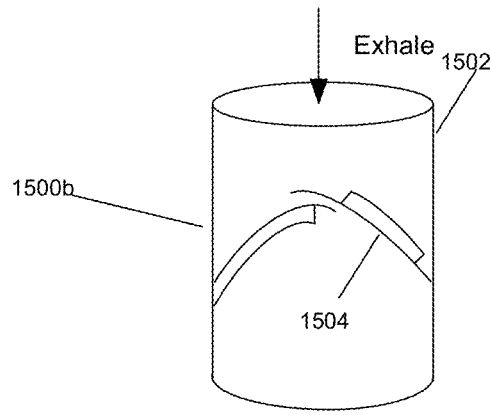
FIG. 15B shows a schematic for a device capable of converting energy from breathing to electrical energy comprising a piezoelectric element attached to flexible vanes of a one-way valve, during a period in which a user is exhaling.

FIG. 15B shows a schematic for a device capable of converting energy from breathing to electrical energy comprising a piezoelectric element attached to flexible vanes 1504 of a one-way valve 1502, during a period in which a user is exhaling. The power generating module may comprise one or more piezoelectric elements bonded to the flexible vanes of a one-way air valve. During inhalation, the vanes may be in a second configuration 1500b. In this second configuration, the vanes may be configured such that the piezoelectric elements are in an unstressed configuration and do not produce a flow of electric current. Generation of the electric current may recommence when the user starts to inhale and the vanes move into the stressed configuration once again.

The power generating module may be configured to generate electric power during exhalation instead of, or in addition to, during exhalation. For instance, the one-way valve may be configured to be in a stressed configuration during exhalation instead of during inhalation. The power generating module may comprise a first one-way valve configured to generate electric current during inhalation and a second one-way valve configured to generate electric current during exhalation in order to harvest energy from both phases of the breathing cycle.

FIG. 15C shows a schematic for a device capable of converting energy from breathing to electrical energy comprising a piezoelectric element 1508 attached to the surface of an air-carrying tube 1506, during a period in which a user is inhaling. The power generating module may comprise one or more piezoelectric elements bonded to the surface of an air-carrying tube. During inhalation, the tube may be in a first configuration 1500c. In this first configuration, the tube may be configured such that the piezoelectric elements are in a stressed configuration and produce a flow of electric current. The passage of air during inhalation may maintain the tube in the first configuration, allowing an electric current to be generated as long as a user is inhaling.

Figure 15D:
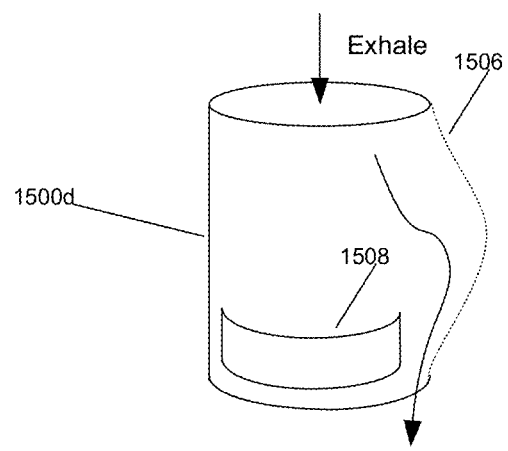
FIG. 15D shows a schematic for a device capable of converting energy from breathing to electrical energy comprising a piezoelectric element attached to the surface of an air-carrying tube, during a period in which a user is exhaling.

FIG. 15D shows a schematic for a device capable of converting energy from breathing to electrical energy comprising a piezoelectric element 1508 attached to the surface of an air-carrying tube 1506, during a period in which a user is exhaling. The power generating module may comprise one or more piezoelectric elements bonded to the surface of an air-carrying tube. During exhalation, the tube may be in a second configuration 1500d. In this second configuration, the tube may be configured such that the piezoelectric elements are in an unstressed configuration and do not produce a flow of electric current. Generation of the electric current may recommence when the user starts to inhale and the tube moves into the stressed configuration once again.

The power generating module may be configured to generate electric power during exhalation instead of, or in addition to, during exhalation. For instance, the tube may be configured to be in a stressed configuration during exhalation instead of during inhalation. The power generating module may comprise a first tube configured to generate electric current during inhalation and a second tube configured to generate electric current during exhalation in order to harvest energy from both phases of the breathing cycle.

Providing natural airflow caused by breathing may obviate the need for devices capable of forcing air into a sensor. Thus, the power generating module may significantly reduce the amount of power needed to operate the sensing module. The use of natural airflow may reduce the power requirements of the sensing module by more than 0.1 W, 0.2 W, 0.3 W, 0.4 W, 0.5 W, 0.6 W, 0.7 W, 0.8 W, 0.9 W, or 1 W compared to a sensor utilizing a fan or a resistive element to move air through the sensor. The reduced power consumption may allow the sensor to operate for a significantly increased lifetime without the need to supply a new battery.

The sensing module may be powered by a wireless charging power source. The sensing module may be powered by an inductive charging power source. The sensing module may be powered by a battery. The air filtration and sensing device may comprise a power consumption module. The power consumption module may be configured to allow the air filtration and sensing device to switch between a low-power power saving mode and a high-power performance mode depending on a user's needs at different points in time.

Figure 16:
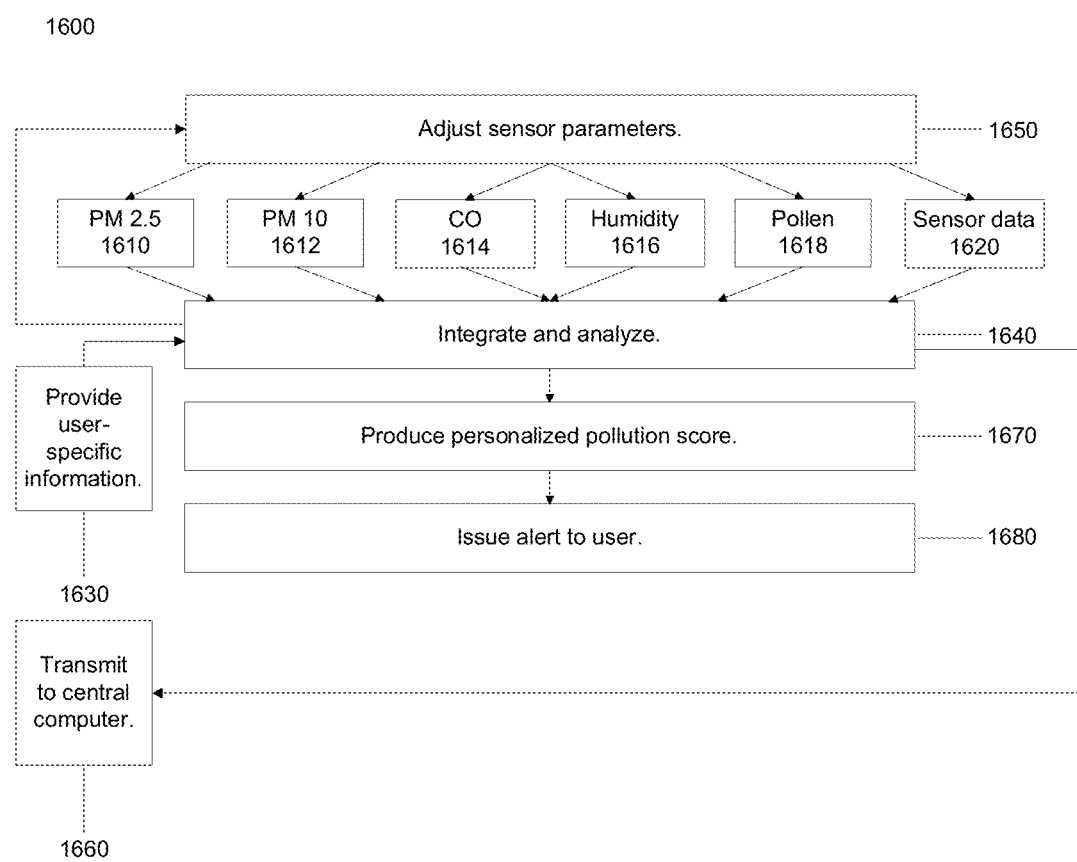
FIG. 16 shows a flowchart for a method of utilizing data from a plurality of sensors to construct a personalized pollution exposure score to a user wearing an air filtration and sensing device.

FIG. 16 shows a flowchart for a method of utilizing data from a plurality of sensors to construct a personalized pollution exposure score to a user wearing an air filtration and sensing device. The method 1600 may comprise the steps of obtaining a PM2.5 measurement, obtaining a PM10 measurement, obtaining a CO measurement, obtaining a humidity measurement, obtaining a pollen measurement, obtaining other sensor data, providing user-specific information, integrating and analyzing the sensor data and user-specific information, adjusting sensor parameters, transmitting to a central computer, producing a personalized pollution score, and issuing an alert to a user.

In step 1610, a PM2.5 measurement is made. The PM2.5 measurement may be made by the sensing module utilizing any air pollution sensor as described herein. In step 1612, a PM10 measurement is made. The PM10 measurement may be made by the sensing module utilizing any air pollution sensor as described herein. In step 1614, a CO measurement is made. The CO measurement may be made by the sensing module utilizing any air pollution sensor as described herein. In step 1616, a humidity measurement is made. The humidity measurement may be made by the sensing module utilizing any humidity sensor as described herein. In step 1618, a pollen measurement is made. The pollen measurement may be made by the sensing module utilizing any air pollution sensor as described herein. In step 1620, additional sensor measurements are made. The additional sensor measurements may be made by the sensing module utilizing any sensor as described herein.

One or more of steps 1610, 1612, 1614, 1616, 1618, or 1620 may further comprise sensor calibration. For instance, one or more of steps 1610, 1612, 1614, 1616, 1618, or 1620 may comprise calibrating a sensor against a baseline sensor or baseline reference, checking whether the sensor is operating normally, determining if the sensor is defective or faulty, and/or correcting for sensor drift, sensor error, or sensor bias. The sensor calibration may be automated. The sensor calibration may be performed dynamically.

One or more of steps 1610, 1612, 1614, 1616, 1618, or 1620 may comprise collecting sensor data. For instance, one or more of steps 1610, 1612, 1614, 1616, 1618, or 1620 may comprise setting a sampling rate, sampling frequency, or accuracy of the sensor.

One or more of steps 1610, 1612, 1614, 1616, 1618, or 1620 may comprise cross-checking an accuracy of the sensor data against other types of sensor data. For instance, one or more of steps 1610, 1612, 1614, 1616, 1618, or 1620 may comprise correlating sensor data from different sensors within the sensing module, correlating sensor data with external sensors (e.g. sensors at weather stations), assigning weights to the data obtained by a sensor based on its accuracy, and/or discarding inaccurate or unreliable sensor data or flagging such sensor data for further analysis. One or more of steps 1610, 1612, 1614, 1616, 1618, or 1620 may comprise employing statistical analysis procedures (e.g. a Mahalanobis distance or Euclidean distance) to determine a sensor accuracy.

In step 1630, user-specific information is provided. The user-specific information may comprise one or more of the user's age, gender, location, height, weight, body mass index (BMI), body composition information (such as body fat content), health status (such as ongoing medical conditions like allergies, high blood pressure, or other medical disorders), and personal preferences as to level of protection desired. The user-specific information may comprise any user-specific information as may be useful in determining a personalized pollution score, as described herein.

In step 1640, the sensor data and user-specific information are integrated and analyzed. Step 1640 may comprise sensor fusion of different sensor data to, for instance, compensate for certain inherent deficiencies of individual sensors. For instance, step 1640 may comprise applying one or more filters. The filters may comprise Kalman filters. The filters may comprise higher-order filters. The filters may comprise any filter as is known to one having skill in the art.

The sensor data may be analyzed using a variety of devices in a variety of locations. For instance, the sensor data may be analyzed on a user's mobile device, such as a user's smartphone, tablet computer, laptop computer, or any other portable electronic device. The sensor data may be analyzed on a user's wearable device, such as a user's smartwatch. The sensor data may be analyzed at a remote server. The remote server may further perform aggregation of sensor data for multiple users within the same geographic location or across different geographic locations. The aggregated sensor data may allow for the creation of crowd-sourced pollution data in a variety of geographic locations.

In some embodiments, step 1640 may further comprise the compression and/or storage of raw or analyzed sensor data. The compressed sensor data may be compressed and/or stored on a user's mobile device, such as a user's smartphone, tablet computer, laptop computer, or any other portable electronic device. The compressed sensor data may be compressed and/or stored on a user's wearable device, such as a user's smartwatch. The compressed sensor data may be compressed and/or stored at a remote server. The compressed sensor data may be compressed and/or stored using any data compression and/or storage technique as is known to one having skill in the art. The compressed sensor data may require less than 2, less than 5, less than 10, less than 20, less than 50, less than 100, less than 200, less than 500, or less than 1000 times as much storage space as the uncompressed raw sensor data.

In some embodiments, step 1640 may further comprise the transmission of the analyzed data to a user's mobile device, such as a user's smartphone, tablet computer, laptop computer, or any other portable electronic device. The transmission may be via a wired communication channel. The transmission may be via a wireless communication channel. The wireless communication may be via Bluetooth communication. The wireless communication may be via Wi-Fi communication. The wireless communication may be via any other wireless communication known to one having skill in the art.

In step 1650, the results of the integration and analysis procedure are utilized to adjust one or more sensor parameters if necessary. For instance, one or more sensors of the sensing module may be selectively activated or deactivated. One or more sensors of the sensing module may have its sensitivity adjusted. One or more sensors of the sensing module may have its dynamic range adjusted. One or more sensors of the sensing module may have its sampling rate adjusted. One or more sensors of the sensing module may be reconfigured to collect more or less data. For example, a person moving though a city with spatially variable pollution may be likely to benefit from more frequent measurement of pollution, at the cost of the sensing system consuming more energy. By contrast, if the person is sitting in a park (as revealed by GPS position and velocity data) and the wind-speed (as reported by local fixed measurement stations) is low, the PM2.5 pollution sensor may not need to be polled as frequently or could even be turned off, saving energy.

Step 1650 may also comprise the programming and/or customization of sensors to provide personalized sensor settings. For instance, one or more sensors may be programmed to detect a particular pollutant with a greater or lesser sensitivity based on a user's physiological needs (such as health status, medical condition, or allergies), activities (such as participation in athletic endeavors or commuting to work), and/or local environment (such as geographic location, proximity to known sources of pollution, time of day, season, etc). As an example, a user who is allergic to a particular allergen may utilize a sensor that is programmed to detect the allergen with very high sensitivity. In contrast, a user who is not allergic to the allergen may utilize a sensor that is programmed to detect the allergen with very low sensitivity. The sensors can be preprogrammed prior to use, by a user or by another entity.

In step 1660, the results of the integration and analysis procedure are transmitted to a central computer (e.g., a server). The central computer may store additional information that may be beneficial to determining a user's personalized pollution score, as described herein. For instance, the central computer may store pollution data from other sources such as fixed roof-top sensors and other humans wearing mobile sensors. The measurements from one or more sensors of the sensing module may be conveyed to the central computer, where the values are compared with other data sources such as pollution levels reported from fixed monitoring stations or other people wearing pollution sensors. The central computer may aggregate the data and utilize statistical techniques to identify individual sensor systems that are reporting unreliable and/or incorrect values. Gradual or sudden changes in the signal output of any one sensor may therefore be remotely detected. Depending on the nature of the discrepancy and the fault, this information may be used to take corrective actions. For example, when the central computer detects sensing defects, a replacement sensor system may be sent to a user. Alternatively, the central computer may send a new set of calibration data, allowing it to be applied to the local sensors to maintain or improve sensing performance.

In step 1670, a personalized pollution score is produced. The personalized pollution score may be produced by combining local and cloud data to produce data bearing on the health of a user. For instance, information from a pressure sensor and a geometrically defined aperture may be combined to determine the amount of air entering the human lung. By integrating this volumetric flow over time, it may be possible to obtain an estimate of the total amount of air that has moved into the lung in a given time period, such as minute, day, week, month, or year. By combining this information with pollution data obtained from local or remote sensor data (such as a pollution sensor of the sensing module or local pollution data obtained from a cloud-based storage system), the cumulative pollution exposure of the individual may be calculated. The cumulative exposure may be calculated as the product of the total air volume and the measured or estimated local pollution level. The cumulative exposure $E_{cumul}(t)$ may be calculated at each time point t according to:

$$E_{cumul}(t) = \int_0^t V_{inhale}(t') * P(t',l) dt'$$

Here, $V_{inhale}(t')$ is the instantaneous volume of air inhaled and $P(t', l)$ is the instantaneous local pollution level at the location l.

The personalized pollution score may account for variations in filtration performance of the filter over time. For instance, the cumulative exposure may be calculated by factoring in the filter performance:

$$E_{cumul}(t) = \partial_0^t V_{ihale}(t') * P(t',l) * \eta(t') dt'$$

Here, $\eta(t')$ is the instantaneous filtration capture performance ranging from 0 to 1 relative to some baseline.

The personalized pollution score may account for personal medical information. For instance, the personalized pollution score may be calculated using only information about a person's exposure to a particular pollutant, such as an allergen. As an example, a personalized pollen exposure $E_{poll}(t)$ may be calculated according to:

$$E_{poll}(t) = \partial_0^t V_{inhale}(t') * P_{poll}(t',l) * \eta_{poll}(t') dt'$$

Here, $P_{poll}(t', l)$ is the instantaneous local pollen level at location l and $\eta_{poll}(t')$ is the instantaneous pollen filter capture performance.

The personalized pollution score may combine two or more health-relevant parameters, such as both PM 2.5 levels and personal medical information, such as an allergic condition. For instance, for a person with allergies who also wishes to minimize pollution, the PM 2.5 exposure and allergen exposure may be combined to calculate a weighted total exposure according to:

$$E_{total}(t) = \partial_0{}^t V_{inhale}(t')(w_{PM2.5} - w_{poll}) P_{PM2.5}(t', l) \eta_{PM2.5}(t') w_{poll} P_{poll}(t', l) \eta_{poll}(t', l) dt'$$

Here, $w_{PM2.5}$ is a weighting factor for PM 2.5, $w_{poll}$ is a weighting factor for pollen, $P_{PM2.5}(t', 1)$ is the instantaneous PM 2.5 level at location 1, and $\eta_{PM2.5}(t')$ is the instantaneous PM 2.5 filter capture performance.

The personalized exposure metrics may be combined with epidemiological and clinical data to provide estimates of the amount of life time gained by using the filtration device. For example, if lifelong exposure to polluted air in a city reduces the mean life expectancy of 75 years (in the absence of pollution) by 15 years, an estimate of the life seconds gained by avoiding a pollutant for a period of 100 hours per year given a filtration efficiency of 80% may be calculated as follows:

Health effect of pollution=reduction of life expectancy/life expectancy without pollutant=15/75=0.2.

Duration of filter usage per year=100 hours.

Estimated reduction of life expectancy without filter=100*0.2=20 hours.

Estimated reduction of life expectancy with filter=100*0.2*(1-filtration performance)=4 hours.

Estimated life seconds gained this year by using filter= (20−4)*3600=57600 seconds.

In step 1680, an alert is issued to the user. The alert may be issued if the integration and analysis procedure determines that an action must be taken by the user. For instance, improper sensor readings may indicate the air filtration and sensing system is improperly positioned within a user's nose. In such case, the user may be prompted to reseat/adjust the position of an air-filtering device present in his/her nasal cavity. The alert may comprise an audible, visible, or tactile alert. For instance, the alert may comprise a sound played on the user's smartphone or other portable electronic device, a message or graphic displayed on screen of the user's smartphone or other portable electronic device, and/or a vibration of the user's smartphone or portable electronic device. The alert may comprise an indication of the number of life seconds, life hours, life days, life months, or life years that a person has gained by using the filter.

A person of ordinary skill in the art will recognize many variations, alterations and adaptations based on the disclosure provided herein. For example, the order of the steps of the method 1600 can be changed, some of the steps removed, some of the steps duplicated, and additional steps added as appropriate. Some of the steps may comprise sub-steps. Some of the steps may be automated and some of the steps may be manual. The processor as described herein may comprise one or more instructions to perform at least a portion of one or more steps of the method 1600.

The sensing analysis module described herein may contain software instruction, algorithms, or sets of instructions to provide predictive analytics relating to air pollution conditions. For instance, the sensing analysis module may be configured to predict whether one or more pollutant levels are likely to increase or decrease. The sensing analysis module may be configured to predict a rate of increase or decrease in the pollutant levels. The sensing analysis module may be configured to predict which types of pollutants are likely to be present at a given time and in a given location based, for instance, on the current or predicted future weather conditions, the season, or the time of day.

The sensing analysis module may be configured to search for information on databases (such as the NCBI PubMed database, Google Scholar, or any other database) related to pollutants and their impact on human health. Using these database sources, the sensing analysis module may be configured to predict the impact of pollution to a user (for instance, by providing a "pollution score" or a "health score" to the user based upon the pollution in their area and the functionality of their filter), warn the user of imminent harm that may result from continued ingestion of polluted air, and/or provide recommendations of corrective action by the user. For instance, the sensing analysis module may suggest that the user utilize a different travel route, relocate to a different area, reduce or cease physical activity, utilize additional filtration protection, or switch filters. In some cases, the sensing module may suggest that the user administer a medication. For instance, the sensing module may suggest that the user utilize an inhaler or a nasal spray.

The sensing analysis module may arrive at health conclusions utilizing adaptive learning models. For instance, the sensing analysis module may utilize machine learning models, including supervising learning models, semi-supervised learning models, and/or unsupervised learning models. The sensing analysis module may utilize statistical techniques such as principal components analysis or convolutional neural networks. These models may be employed to infer which pollutants are of particular concern to a user. The models may be dynamically adjusted according to changes in a user's condition, such as the worsening of an allergy.

Figure 17:
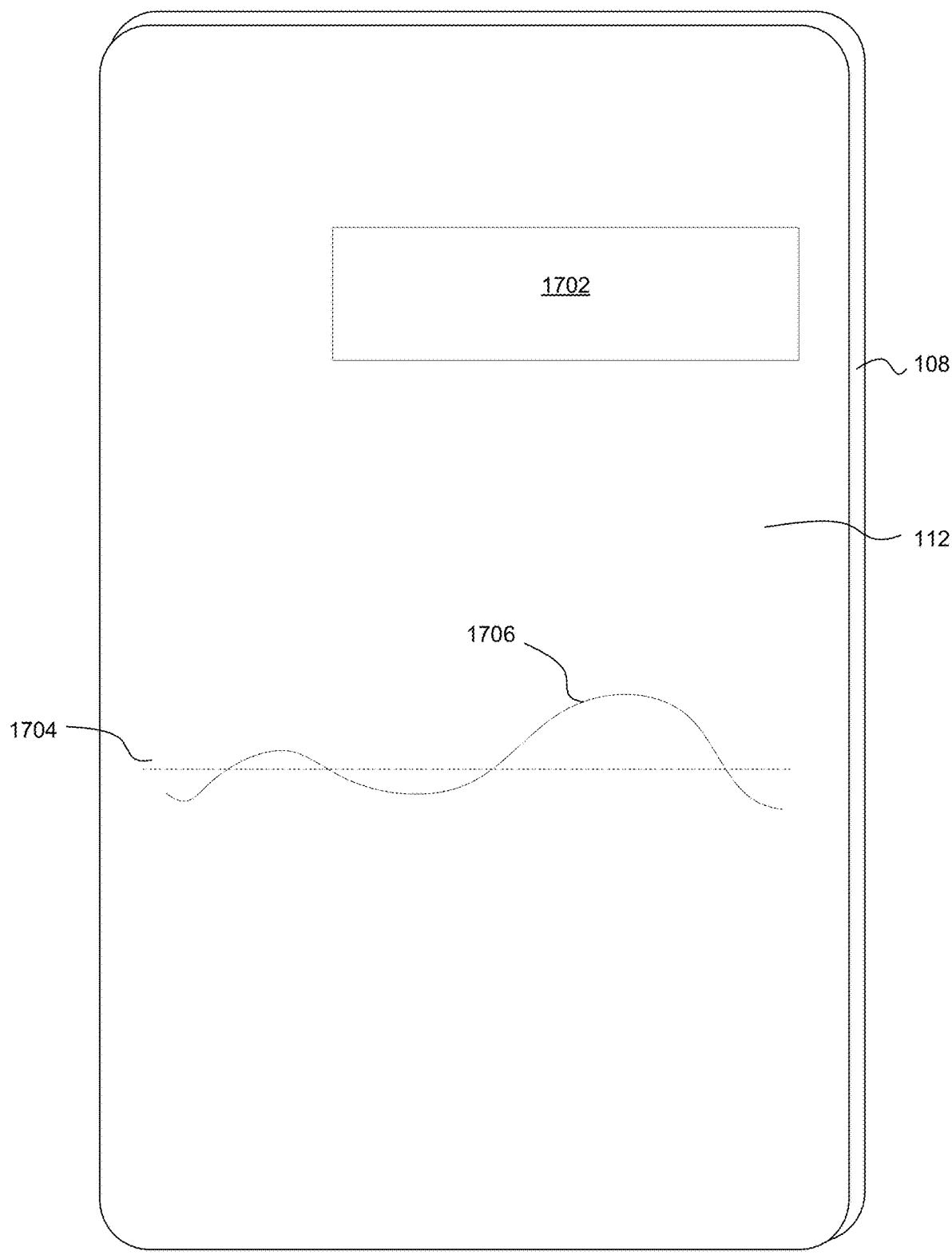
FIG. 17 shows a graphical user interface for use with an air filtration and sensing device that displays a user's pollution exposure while using the device and the user's expected exposure without the device.

In some embodiments, the sensing analysis module can generate one or more graphical user interfaces (GUIs) for displaying a plurality of pollution and health metrics. The GUIs may be rendered on a display screen on a user device. A GUI is a type of interface that allows users to interact with electronic devices through graphical icons and visual indicators such as secondary notation, as opposed to text-based interfaces, typed command labels or text navigation. The actions in a GUI are usually performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be displayed on a user device (e.g., on graphical display 112 of user device 120 in FIG. 1). The GUIs may be provided through a mobile application. Examples of such GUIs are illustrated in FIGS. 17 through 20 and described as follows FIG. 17 shows a graphical user interface for use with an air filtration and sensing device that displays a user's pollution exposure while using the device and the user's expected exposure without the device. The user's current location 1702 may be displayed. Additionally, pollution metrics may be displayed on the GUI. These metrics may include changes in pollution levels 1706 (e.g., of certain pollutants) plotted as a function of time relative to a safe level 1704. In some cases, the metrics may indicate fluctuations in levels of a plurality of different types of pollutants. In some embodiments, the relative reduction (e.g., percentage reduction) in the user's exposure to the pollutants (using the exemplary pollution filtration and sensing device described herein) may be displayed in the GUI. Other metrics, for example the user's breathing rate and heart rate may also be displayed in the GUI.

Figure 18:
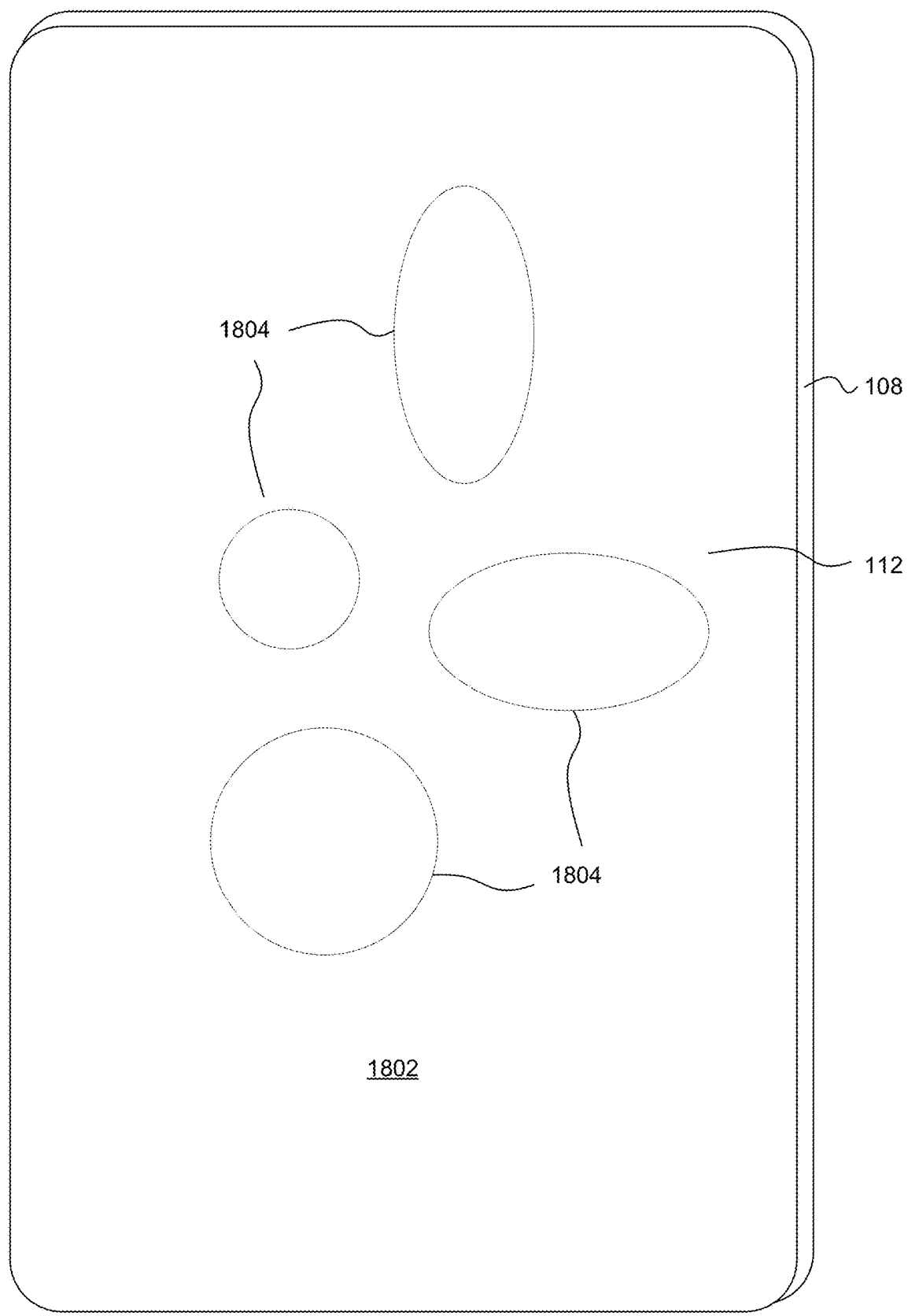
FIG. 18 shows a graphical user interface for use with an air filtration and sensing device that displays pollution exposure levels in different locations near a user.

FIG. 18 shows a graphical user interface for use with an air filtration and sensing device that displays pollution levels in different locations near a user. The GUI may include a map 1802. The map may include a 2D map, such as an overhead map. The map may include a 3D map. The 3D map may be alterable to view the 3D environment from various angles. Solid renderings, wireframes, or other types of imaging may be shown, as described previously herein. Locations having high pollution levels may be indicated on the map, for example using various graphical objects (e.g., a circle) 1804. Any shape and/or size of the graphical objects may be contemplated. A radius of the circles may be representative of the area extent of the pollution. For example, a larger circle may indicate that a larger region is affected by the pollution, whereas a smaller circle may indicate that a smaller region is affected by the pollution. Different colors and/or shading may be used to differentiate the pollution levels within each region. The colors can be provided as discrete colors or along a gradient. As an example, red color may be used to indicate that an area is experiencing severe air pollution, whereas yellow color may be used to indicate that another area is experiencing mild to moderate air pollution. Any color scheme or any other visual differentiation scheme may be contemplated. In some embodiments, the GUI may include a text box that notifies the user about the current level of pollution in the area where the user is located. The level of pollution in the area (where the user is located) may be provided relative to other areas, for example as a relative percentage value.

Figure 19:
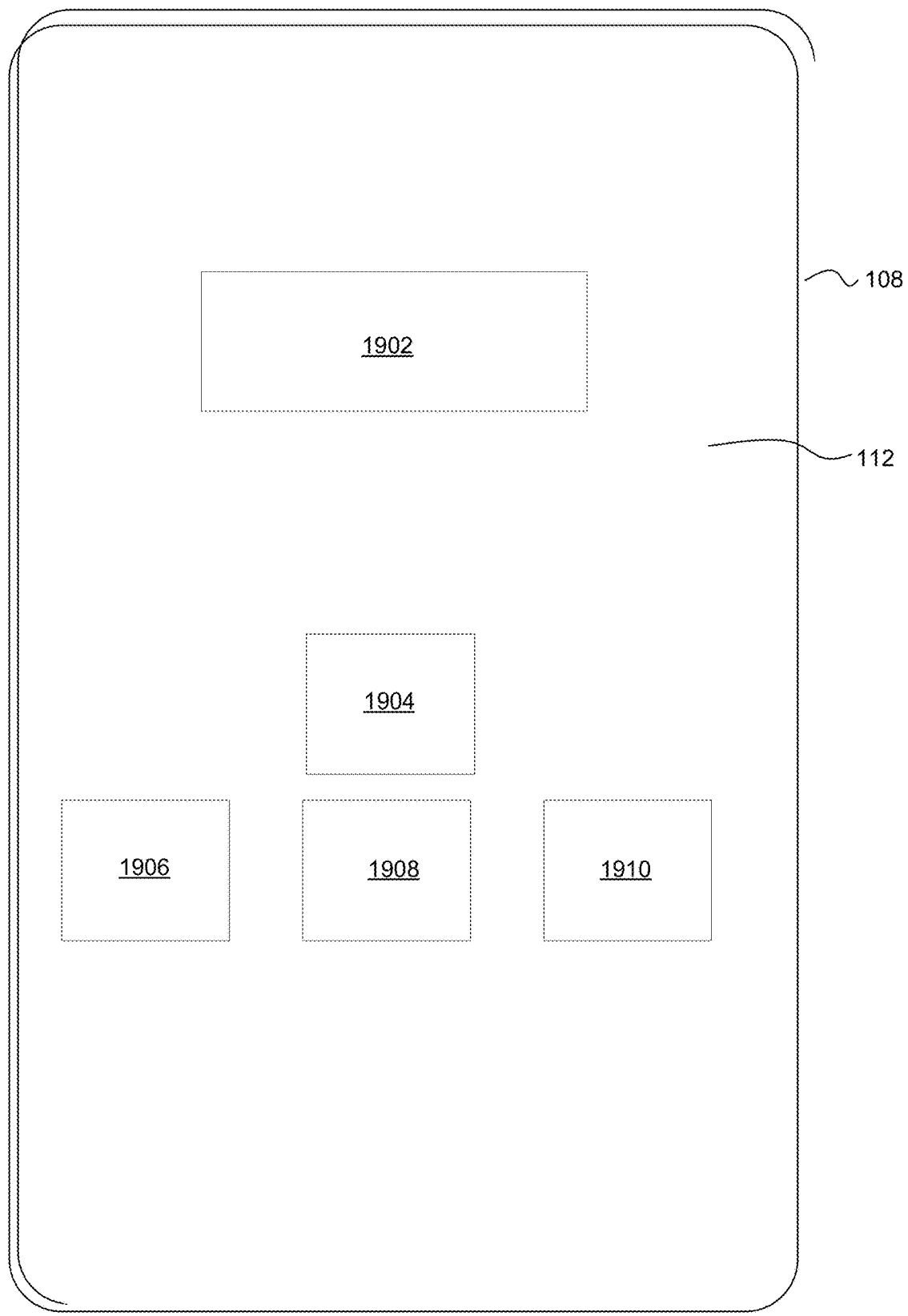
FIG. 19 shows a graphical user interface for use with an air filtration and sensing device that displays a user's pollution exposure score.

FIG. 19 shows a graphical user interface for use with an air filtration and sensing device that displays a user's pollution exposure score. The GUI may display a numerical value 1902 that is indicative of the predicted impact of the pollutants on the user's health. A pollution rating 1904 (e.g., "fair") may also be displayed along with the numerical value. Other metrics may also be displayed, e.g., temperature 1906 of the surrounding environment, filter health 1908 showing the remaining life and/or filtering performance of the device, and power level 1910 of the device. Additionally, a user can also view the pollution ratings and corresponding numerical values of other different users within the user's social circle.

In some embodiments, the graphical user interface may display the air quality at a location near a user as a function of time. The GUI may include a heading and a display of daily air quality levels in a particular locality. Different colors and/or shading may be used to differentiate the air quality at different points in time during the day. The colors can be provided as discrete colors or along a gradient. As an example, red color may be used to indicate that an area is experiencing severe air pollution, whereas yellow color may be used to indicate that another area is experiencing mild to moderate air pollution. Any color scheme or any other visual differentiation scheme may be contemplated. In some embodiments, the GUI may include display daily air quality levels in a particular locality for the past week, for instance, on the most recent Thursday, most recent Saturday, etc. The change in air quality levels may be observed over any period of time (e.g., by hour, week, month, quarter, season, year, etc.) and/or region. In some embodiments, the GUI may permit the user to specify any temporal range and/or geographical location of interest.

Figure 20B:
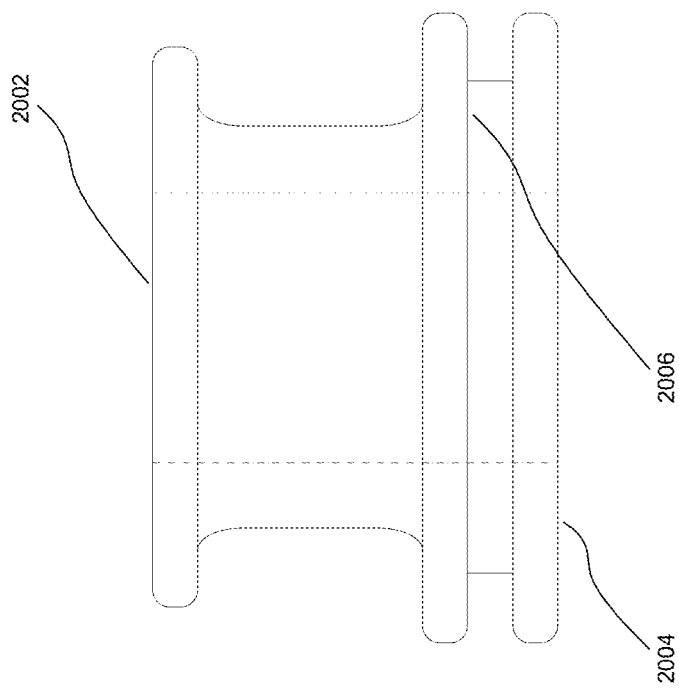
FIG. 20B shows a cross-sectional view of the air nosebud of FIG. 20A.
Figure 20A:
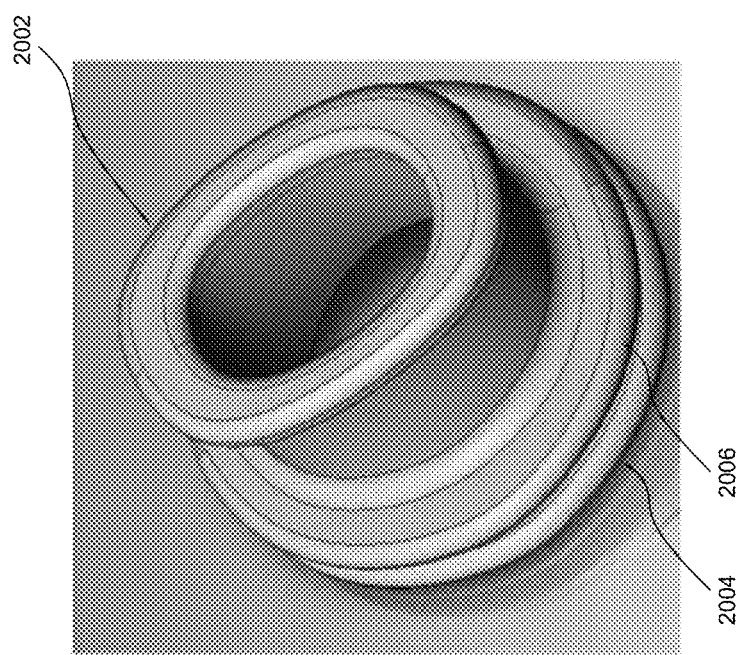
FIG. 20A shows a perspective view of a nosebud that can be used in an air filtration and sensing device.

FIG. 20A shows a perspective view of a nosebud that can be used in an air filtration and sensing device. The nosebud may comprise an upper lip 2002 and lower lips 2004 and 2006. The upper and lower lips may be configured to engage natural pockets located within the nasal passages, as described later herein. FIG. 20B shows a cross-sectional view of the nosebud retention mechanism of FIG. 20A.

FIGS. 21A-D illustrate exemplary dimensions of a nosebud that can be used in an air filtration and sensing device. For example, FIG. 21A shows a top view of a nosebud. FIG. 21B shows a first cross-sectional view of the nosebud. FIG. 21C shows a second cross-sectional view of the nosebud when it is retained in the septum of the nasal passageway. The opening of the nosebud can be formed having different dimensions, for example as shown in FIG. 21D.

FIG. 22A shows a magnetic resonance image (MRI) of pockets within the nose that may accept an air filtration and sensing device comprising a nosebud. As seen in FIG. 22A, the nasal passages have natural pockets 2200 that lie directly above the nostril. These pockets may serve as anchoring points for retaining the nosebud of the air filtration and sensing device.

FIG. 22B shows an air filtration and sensing device comprising a nosebud that is anchored in the pockets of the nose. The nosebud may include a retention mechanism. The retention mechanism may comprise an upper lip 2002 and lower lips 2004 and 2006. The upper and lower lips may be configured to engage the natural pockets 2200 to anchor the nosebud in place in the user's nasal passages, without requiring the use of one or more external fixation devices to secure the nosebud from outside of the user's nasal passages.

FIG. 22C shows a first step of inserting a nosebud of an air filtration and sensing device into the nose. The nosebud may be inserted into the nose at an angle in order to slide past the cartilaginous structures of the nostril. The nosebud may be made of a flexible material, such as an organic polymer. The flexible material may allow the nosebud to be compressed into a smaller volume as it is inserted into the nostril, to aid in moving past the cartilaginous structures of the nostril.

FIG. 2D shows a second step of inserting the nosebud into the nose. The second step may comprise rotating the nosebud in a front-to-back motion to move past the cartilaginous structures of the nostril.

FIG. 22E shows a third step of inserting the nosebud into the user's nose. The third step may comprise anchoring the nosebud in the natural pockets of the user's nasal passage. Once the nosebud is in place in the user's nasal passages, the compression force is released. This causes the flexible material to expand to its original shape and/or size to fill at least a portion of the nasal passages, thereby anchoring the nosebud. Accordingly, the nosebud can be affixed in place in the user's nasal passages, and can maintain a desired position without requiring the use of one or more external fixation devices to secure the nosebud from outside of the user's nasal passages.

In some cases, the nosebuds may have a size and shape that is customized to fit a user's nasal passages. For instance, the nosebuds may have a size and shape that fills a majority of the user's nasal passage. The nosebuds may fill more than 50%, more than 60%, more than 70%, more than 80%, more than 90%, more than 95%, or more than 99% of a user's nasal passage. The nosebuds may comprise a sealing edge. The sealing edge may be configured to allow seating of the nosebud at the narrowest portion of the user's nasal passage during inhalation. The sealing edge may prevent leakage of air past the nosebud during inhalation. In some cases, the sealing edge may allow partial leakage of air during exhalation. In this manner, the resistance to airflow during exhalation may be decreased.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An air filtration and analysis system, comprising:
an apparatus configured to be worn by a user, said apparatus comprising a filtration device configured to reduce one or more elements from air prior to inhalation of the air by the user, wherein the apparatus comprises a retention mechanism configured to releasably couple to a nasal passage of the user in order to secure the apparatus in place when worn by the user, wherein the retention mechanism comprises a flexible compressible material that is (i) initially provided in a compressed state to aid insertion of the retention mechanism into the nasal passage and (ii) released from the compressed state into an expanded state to couple the retention mechanism to the nasal passage, and wherein the retention mechanism comprises an upper lip and at least one lower lip that are configured to anchor to natural pockets of the nasal passage;
a plurality of sensors comprising a first sensor, a second sensor, and a third sensor, wherein the first and second sensors are located on the apparatus and the third sensor is located remote from the apparatus, wherein the first sensor is configured to collect a first set of data associated with air inhaled by the user as said air passes through the apparatus into the user's body, wherein the second sensor is configured to collect a second set of data associated with breath exhaled by the user as said breath passes through the apparatus out of the user's body, and wherein the third sensor is configured to collect a third set of data associated with an environment in which the user is located; and
a processor configured to analyze (1) the first set of data to determine one or more characteristics of the air inhaled by the user, (2) the second set of data to determine a health status or medical conditions of the user based on the breath exhaled by the user, and (3) the third set of data to determine one or more characteristics of the air in the environment,
wherein the processor is further configured to generate recommendations for improving a health or well-being of the user based on the analyzed first, second, and third sets of data, and wherein the recommendations comprise a score provided on a scale, the score being indicative of a predicted impact level of the one or more elements on the user's health.

2. The system of claim 1, wherein the filtration device is configured to be placed within the nasal passage of the user.

3. The system of claim 1, wherein the first sensor and the second sensor are selected from the group consisting of chemical sensors, pressure sensors, and air flow sensors, and wherein the third sensor is selected from the group consisting of heart-rate monitors, blood oxygen saturation sensors, global positioning system (GPS) sensors, temperature sensors, and inertial sensors.

4. The system of claim 1, wherein the processor is further configured to control operation of the filtration device to reduce an impact of the one or more elements on the user's health.

5. The system of claim 1, wherein the processor is configured to perform one or more of the following steps: (1) calibrate the first sensor or the second sensor against a baseline sensor reference; (2) check whether the first sensor or the second sensor is operating normally; and/or (3) correct for sensor drift, error or bias in the first sensor or the second sensor.

6. The system of claim 1, wherein the first and second sensors are configured to collect the first and second sets of data at different predetermined sampling frequencies.

7. The system of claim 1, wherein the processor is configured to data cross-check an accuracy of the first, second, and third sets of data against each other.

8. The system of claim 1, wherein the processor is configured to determine correlations between the first, second, and third sets of data.

9. The system of claim 1, wherein the processor is configured to assign weights to the first, second, and third sets of data based on an accuracy of each of the first, second, and third sensors.

10. The system of claim 1, wherein the processor is configured to analyze the first, second, and third sets of data using statistical methods.

11. The system of claim 1, wherein the first, second, and third sets of data each comprises a different type of data.

12. The system of claim 1, wherein the processor is located on a mobile device or a wearable device that is carried or worn by the user, and/or on a server that is remote to the user.

13. The system of claim 12, wherein the score comprises a numerical value that is displayable on a graphical user interface of the mobile device or the wearable device.

14. The system of claim 1, wherein the processor is configured to compress and store the first, second, and third sets of data in a memory.

15. The system of claim 1, wherein the processor is configured to control the filtration device (1) to meet the user's physiological needs and activities, and (2) based on the user's local environment.

16. The system of claim 1, wherein the processor is further configured to analyze the second set of data to determine a type of activity that the user is performing.

17. The system of claim 1, wherein the processor is configured to analyze the first and third sets of data to determine the user's proximity to known sources of pollution, the environment that the user is located in, time of day, or the season that the user is currently in.

18. The system of claim 17, wherein the processor is configured to control the filtration device to dynamically and automatically adapt in real-time as the user moves from one location to another location, as the time of day changes, as the season changes, or depending on changes in the user's health status.

19. The system of claim 1, wherein the processor is configured to (1) selectively activate or de-activate at least one of the plurality of sensors, or (2) adjust a sensitivity level, sensing range, or sampling frequency of at least one of the plurality of sensors.

20. The system of claim 1, wherein the recommendations further comprise one or more of the following: (1) a warning of an impact to the user's health should the user continue to inhale air containing the one or more elements; and/or (2) a suggested corrective action to minimize inhalation of the air containing the one or more elements, wherein the suggested corrective action comprises a recommendation to the user to relocate from the user's current location to another area with less pollution.

21. The system of claim 1, wherein the recommendations are displayed as a set of graphical visual objects on a graphical display.

22. The system of claim 1, wherein the apparatus has a shape or profile that minimizes physical interference with lip movement of the user and does not visually obstruct lip movement or facial expression of the user, while the apparatus is being worn by the user.

23. The system of claim 22, wherein the apparatus does not encroach on the user's upper lip while the apparatus is being worn by the user.

24. The system of claim 1, wherein the flexible compressible material comprises an organic polymer.

25. The system of claim 1, wherein the retention mechanism comprises a sealing edge configured to seal the nasal passage to prevent the air from bypassing the filtration device during inhalation.

26. A method for air filtering and respiratory analysis, comprising:
   providing an apparatus configured to be worn by a user, said apparatus comprising a filtration device configured to reduce one or more elements from air prior to inhalation of the air by the user, wherein the apparatus comprises a retention mechanism configured to releasably couple to a nasal passage of the user in order to secure the apparatus in place when worn by the user, wherein the retention mechanism comprises a flexible compressible material that is (i) initially provided in a compressed state to aid insertion of the retention mechanism into the nasal passage and (ii) released from the compressed state into an expanded state to couple the retention mechanism to the nasal passage, and wherein the retention mechanism comprises an upper lip and at least one lower lip that are configured to anchor to natural pockets of the nasal passage;
   providing a plurality of sensors comprising a first sensor, a second sensor, and a third sensor, wherein the first and second sensors are located on the apparatus and the third sensor is located remote from the apparatus;
   using the first sensor to collect a first set of data associated with air inhaled by the user as said air passes through the apparatus into the user's body, using the second sensor to collect a second set of data associated with breath exhaled by the user as said breath passes through the apparatus out of the user's body, and using the third sensor to collect a third set of data associated with an environment in which the user is located;
   with aid of a processor:
      analyzing (1) the first set of data to determine one or more characteristics of the air inhaled by the user, (2) the second set of data to determine a health status or medical conditions of the user based on the breath exhaled by the user, and (3) the third set of data to determine one or more characteristics of the air in the environment; and
      generating recommendations for improving a health or well-being of the user based on the analyzed first, second, and third sets of data, wherein the recommendations comprise a score provided on a scale, the score being indicative of a predicted impact level of the one or more elements on the user's health.

27. A tangible computer readable medium storing instructions that, when executed by a processor, causes the processor to perform a computer-implemented method for filtering air and respiratory analysis, the method comprising:
   collecting a first set of data using a first sensor, a second set of data using a second sensor, and a third set of data using a third sensor, wherein the first and second sensors are located on an apparatus configured to be worn by a user, and the third sensor is located remote from the apparatus, said apparatus comprising a filtration device configured to reduce one or more elements from air prior to inhalation of the air by the user, wherein the apparatus comprises a retention mechanism configured to releasably couple to a nasal passage of the user in order to secure the apparatus in place when worn by the user, wherein the retention mechanism comprises a flexible compressible material that is (i) initially provided in a compressed state to aid insertion of the retention mechanism into the nasal passage and (ii) released from the compressed state into an expanded state to couple the retention mechanism to the nasal passage, and wherein the retention mechanism comprises an upper lip and at least one lower lip that are configured to anchor to natural pockets of the nasal passage, wherein the first set of data is associated with air inhaled by the user as said air passes through the apparatus into the user's body, wherein the second set of data is associated with breath exhaled by the user as said breath passes through the apparatus out of the user's body, and wherein the third set of data is associated with an environment in which the user is located; and
   with aid of the processor:
      analyzing (1) the first set of data to determine one or more characteristics of the air inhaled by the user, (2) the second set of data to determine a health status or medical conditions of the user based on the breath exhaled by the user, and (3) the third set of data to determine one or more characteristics of the air in the environment; and
      generating recommendations for improving a health or well-being of the user based on the analyzed first, second, and third sets of data, wherein the recommendations comprise a score provided on a scale, the score being indicative of a predicted impact level of the one or more elements on the user's health.

* * * * *